US012653845B2

(12) United States Patent
Sørum et al.

(10) Patent No.: US 12,653,845 B2
(45) Date of Patent: *Jun. 16, 2026

(54) METHOD FOR TREATING AND/OR PREVENTING A PARASITIC INFECTION IN A TELEOST

(71) Applicant: PREVIWO AS, Oslo (NO)

(72) Inventors: Henning Sørum, Oslo (NO); Kira Salonius, Oslo (NO)

(73) Assignee: PREVIWO AS, Oslo (NO)

( * ) Notice: Subject to any disclaimer, the term of this patent is extended or adjusted under 35 U.S.C. 154(b) by 756 days.

This patent is subject to a terminal disclaimer.

(21) Appl. No.: 17/766,551

(22) PCT Filed: Oct. 2, 2020

(86) PCT No.: PCT/EP2020/077734
§ 371 (c)(1),
(2) Date: Apr. 5, 2022

(87) PCT Pub. No.: WO2021/064217
PCT Pub. Date: Apr. 8, 2021

(65) Prior Publication Data
US 2023/0338437 A1      Oct. 26, 2023

(30) Foreign Application Priority Data

Oct. 5, 2019   (NO) ..................................... 20191193
Oct. 5, 2019   (NO) ..................................... 20191194

(51) Int. Cl.
  *A61K 35/741*        (2015.01)
  *A01K 61/13*         (2017.01)
  (Continued)

(52) U.S. Cl.
  CPC ............ *A61K 35/741* (2013.01); *A01K 61/13* (2017.01); *A61K 45/06* (2013.01); *A61P 33/14* (2018.01); *C12R 2001/38* (2021.05)

(58) Field of Classification Search
  CPC ...... A61K 35/741; A61K 45/06; A01K 61/13; A61P 33/14; C12R 2001/38
  See application file for complete search history.

(56) References Cited

U.S. PATENT DOCUMENTS 11,266,168 B2 *   3/2022   Sørum ................... A01K 61/13
2007/0020328 A1   1/2007   Lin

FOREIGN PATENT DOCUMENTS

WO        2015074946 A1    5/2015
WO        2015155293 A1    10/2015
            (Continued)

OTHER PUBLICATIONS

Lieke, T. et al. (2020), Sustainable aquaculture requires environmental-friendly treatment strategies for fish diseases. Rev Aquacult 12: 943-965. First published online Jul. 23, 2019. (Year: 2019).*

(Continued)

*Primary Examiner* — Daniel E Kolker
*Assistant Examiner* — Bailey M Morgan
(74) *Attorney, Agent, or Firm* — Meunier Carlin & Curfman LLC

(57)                    ABSTRACT

The present document discloses methods and means for treating and/or preventing ectoparasite infestations and/or gill parasite infection in teleosts by the administration of probiotic bacteria to the teleosts.

19 Claims, 6 Drawing Sheets

(51) Int. Cl.

| | |
|---|---|
| *A61K 45/06* | (2006.01) |
| *A61P 33/14* | (2006.01) |
| *C12R 1/38* | (2006.01) |

(56) References Cited

FOREIGN PATENT DOCUMENTS

| | | | | |
|---|---|---|---|---|
| WO | WO-2018007632 A1 * | 1/2018 | ............. | A01K 61/13 |
| WO | WO-2019135009 A1 * | 7/2019 | ............. | A23K 10/18 |

OTHER PUBLICATIONS

International Search Report and Written Opinion, issued by the International Searching Authority (ISA/EP) in PCT Application No. PCT/EP2020/077734 on Feb. 9, 2021. 7 pages.

Klakegg, Øystein, et al. "Improved health and better survival of farmed lumpfish (*Cyclopterus lumpus*) after a probiotic bath with two probiotic strains of Aliivibrio." Aquaculture 518, Dec. 3, 2019. Abstract.

Llewellyn et al., "Parasitism perturbs the mucosal microbiome of Atlantic Salmon", Sci Rep. Mar. 7, 2017;7:43465.

\* cited by examiner

METHOD FOR TREATING AND/OR PREVENTING A PARASITIC INFECTION IN A TELEOST

TECHNICAL FIELD

The present document is directed to combating ectoparasites and gill parasites on teleosts. More particularly, the present document discloses a probiotic composition which prevents and treats ectoparasitic infestations and/or gill parasite infections in teleosts.

BACKGROUND OF THE INVENTION

Fish farming involves raising fish in tanks or enclosures. In aquaculture, freshwater, saltwater or anadromic populations, such as fish, crustaceans and shellfish, are raised under controlled conditions. Mariculture is a sub-branch of aquaculture where marine organisms are cultivated in the open ocean or an enclosed section of the ocean, or alternatively in ponds, tanks and the like filled with seawater.

Teleosts are the largest infraclass of the ray-finned fishes. There are over 26000 species, and they separated from other fish, such as sturgeons and bowfins, around 300 million years ago. The teleosts thus share many biological traits, including skin and mucus. Research indicates that the mucus cells are based on primordially conserved principles that could be common to mammals and fish alike. Within the teleosts and salmonids the skin epidermis should thus have similar properties.

The growth and health of fish raised by intensive aquaculture is dependent on that sufficient oxygen and clean water with optimal levels of carbon dioxide, ammonia and with feasible pH can be provided. Also, a sufficient amount of feed with a high content of protein and a well-balanced supply of amino acids is crucial to obtain a commercially durable result. Attempts to increase the growth of farmed fish have generally focused on changing the contents of the feed used.

Farmed fish are often contained at high population densities which increase the risk for infections by e.g. parasites such as fish lice, intestinal worms, fungi, virus and bacteria.

Sea lice belong to the family of copepods (small crustaceans) within the order Siphonostomatoida, family Caligidae. The two main genera are the *Lepeophtheirus* and *Caligus* genera which infect marine fish. Many sea louse species are specific with regard to host genera. For example, *L. salmonis* has high specificity for salmonids, including farmed Atlantic salmon (*Salmo salar*) but it can also parasitize on other salmonids, including brown trout (sea trout: *Salmo trutta*), Arctic char (*Salvelinus alpinus*), and all species of Pacific salmon.

Sea lice feed on fish, and large numbers of lice on the same fish and, or just a couple of lice on a juvenile fish, can be harmful or fatal. Sea lice are marine ectoparasites (external parasites) that feed on the mucus, epidermal tissue, and blood of host marine fish and can cause fin damage, skin erosion, constant bleeding, and open wounds creating a pathway for other pathogens. More damage may be caused when infected fish jump or scrape along nets in an attempt to dislodge any irritating lice. In addition to the suffering from the fish, wholesalers and consumers prefer to buy fish that are free from sea lice, as infested fish are not aesthetically pleasing. This is of course a great problem in fish farming, but sea lice may also spread from fish farms and infect wild fish.

Sexually mature and fertilized female lice release several hundred eggs by hatching. Free-living stages are referred to as nauplii (2 stages) and the copepodids along with chalimus (2 stages) are stationary/attached. All stages, including the movable stages (pre- and adult lice) feed on skin, mucus, blood on/from the fish and the fish's microbiota.

Ectoparasites are a diverse set of organisms that infest the skin and external orifices of animals. On fish, in addition to the skin, the gills are preferred habitat of many ectoparasites, For teleosts, such as salmonids, turbot, cleaner fish, seabass and seabream, ectoparasites include amoeba, lice, copepods and others.

Treatment and prevention of ectoparasites, like sea lice infestation, generally involve the use of different chemical agents, such as organophosphates, carbamates, pyrethroids, pyrethrins, synergists, insect growth regulating chemicals or avermectins. However, such use is undesirable, e.g. due to the spread of these toxic agents to the environment. Development of drug resistance in the sea lice has terminated the use of chemical delousing in several salmon farming areas and other delousing means as use of freshwater and mechanical delousing has increased in recent years to replace the use of chemical delousing. Increased frequency of delousing in particular with mechanical methods during the warmer season results in more stress, more disease and higher mortality among the farmed salmon.

To protect the wild salmonid species in the salmon farming regions there has been made strict regulations from the governmental authorities to monitor for sea lice infestations weekly and when they appear, to treat any sea lice infestation immediately. In Norway farmed salmonids is mandatorily deloused when the level of sea lice passes 0.1 sea lice per salmon individual, a level of infestation that is not biologically relevant on a mature individual salmon. These regulations result in frequent sea lice treatments which stress the farmed salmon.

Cleaner fish are commonly provided into the aquaculture pens to eat the sea lice from the skin of the primary farmed fish as salmonids. Cleaner fish may be teleosts such as wild caught wrasse species as Goldsinny-wrasse (Ctenolabris rupestris), Ballan wrasse (*Labrus bergylta*) and corkwing wrasse (*Symphodus melops*) or lump fish (*Cyclopterus lumpus*). Recently farming of lump fish for use as cleaner fish has been replacing the wild catch, and farming of Ballan wrasse has also been developed. There is an animal welfare issue linked to the use of cleaner fish since most of the cleaner fish dies in the pens before the salmon reach slaughter size. Little is known about the reasons for the loss of cleaner fish but a large factor is the development of infectious diseases including ulcers, fin rot, metazoan and protistan parasites and also ectoparasites.

The use of cleaner fish reduces the need of chemical or mechanical delousing episodes efficiently, but not fully and if delousing occurs by chemical, mechanical or thermal delousing the cleaner fish may die.

The economical impact of sea lice infestations and the need of delousing has doubled the production costs from 1.5 to 3 euro per kilo Atlantic salmon produced the last 20 years in Norway.

An object of the present invention is thus to overcome or at least mitigate some of the problems described above.

SUMMARY

The present document is directed to a probiotic composition comprising probiotic bacteria of the species *Aliivibrio njordis* and/or *Aliivibrio balderis*, and optionally *Aliivibrio* nannie, for use in the treatment and/or prevention of an ectoparasitic infestation and/or gill parasite infection in a teleost.

The probiotic composition may further comprise probiotic bacteria of the species *Psychrobacter* piscimesodermis, *Psychrobacter* piscimesenchymalis, *Psychrobacter* piscisubcutanea, *Pseudomonas* salmosubcutaneae, *Pseudomonas* salmosubpectoralis and/or *Pseudomonas* salmointermuscularis.

The present document also discloses a probiotic composition comprising probiotic bacteria of the species *Aliivibrio njordis* and/or *Aliivibrio balderis*, and optionally *Aliivibrio nannie* for use in the treatment and/or prevention of an ectoparasitic infestation and/or gill parasite infection in a teleost, wherein said probiotic composition is administered to said teleost before, during or after administration of one or more further probiotic composition(s) comprising one or more of a probiotic bacterium selected from the group consisting of bacteria of the species *Psychrobacter* piscimesodermis, *Psychrobacter* piscimesenchymalis, *Psychrobacter* piscisubcutanea, *Pseudomonas* salmosubcutaneae, *Pseudomonas* salmosubpectoralis and/or *Pseudomonas* salmointermuscularis.

The probiotic composition may comprise probiotic bacteria of two or more different strains of the same bacterial species.

The teleost may be a marine teleost or a fresh water teleost.

The teleost may be of the family Salmonidae, such as salmon, trout, and chars. The teleost of the family Salmonidae may e.g. be Atlantic salmon (*Salmo salar*), brown trout (sea trout: *Salmo trutta*), Arctic char (*Salvelinus alpinus*), and/or any species of Pacific salmon, such as Coho (Silver) salmon (*Oncorhynchus kisutch*), Chinook (King) (*Oncorhynchus tshawytscha*), pink (Humpy) salmon (*Oncorhynchus gorbuscha*), chum (Dog) salmon (*Oncorhynchus keta*), sockeye (*Oncorhynchus nerka*), cutthroat (*Oncorhynchus clarki clarki*) and steelhead (rainbow trout) (*Oncorhynchus mykiss*).

The teleost may also be Atlantic cod, cleaner fish like lump fish and wrasses and freshwater fish as carps and perch.

The ectoparasitic infestation may be caused by an ectoparasite of the genera *Lepeophtheirus*, such as *L. salmonis*, and/or *Caligus*, such as *C. rogercresseyi* and/or *C. elongatus*. Although of different genera, these are commonly referred to as "sealice".

The ectoparasitic infestation may also be caused by an amoeba, such as an amoeba of the genus Neoparamoeba, such as Neoparamoeba perurans, an ectoparasite of the genus *Gyrodactylus*, such as *Gyrodactylus salaris*, an ectoparasite of the genus Cryptocaryon, such as Cryptocaryon *irritans*, an ectoparasite of the genus *Lernaeocera*, such as *Lernaeocera branchialis*, an ectoparasite of the genus *Pseudorhabdosynochus*, and/or an ectoparasite of the genus Amyloodinium.

The probiotic composition may be administered in combination with a chemical parasitic infection treatment agent, such as an organophosphate, a carbamate, a pyrethroid, a payrethrin, a synergist, an insect growth regulating chemical and/or an avermectin.

The probiotic composition may be administered via bath or dip administration in salt, fresh or brackish water, by oral administration, or injection, such as bath administration for a time period of 1 second to 5 hours, such as 1 second to 2 hours, such as 1 seconds to 1 hour, such as 30 seconds to 1 hour or 1 minute to 30 minutes.

The probiotic composition may be administered at least 10 days, such as at least 15 days, 20 days, 25 days, 30 days, or 40 days, before exposure of the teleost to the ectoparasite and/or gill parasite.

Other features and advantages of the invention will be apparent from the following detailed description, drawings, examples, and from the claims.

Definitions

Ectoparasites of teleosts attaching to the skin and/or gills comprise:

Family Caligidae with many different genera (37) with close to 600 species. Genus *Lepeophtheirus* with 162 species with *L. salmonis* as the most important for salmonids. Genus *Caligus* with 268 species with *C. elongatus* Norway (mostly Northern Norway) and Northern Atlantic and *C. rogercresseyi* (Pacific coasts including Chile and British Columbia).

*Gyrodactylus salaris* is a freshwater parasite of salmonids in river systems and for farming of any salmonid in a freshwater facility with water from infected river water it may be beneficial to use probiotics when the breeding stock individuals are taken from marine water.

Cryptocaryon *irritans* is a marine parasite on the skin of fish living in seawater.

*Lernaeocera branchialis* is a copepode parasite of the gills of cod and other marine fish in the northern Atlantic Ocean.

*Pseudorhabdosynochus* spp. parasites of the gills of marine fish in warmer climates mainly farmed grouper fish may be affected.

Amyloodinium spp. infects the skin of marine fish.

Parasites causing gill disease in teleosts are e.g. Neoparamoeba perurans causing amoebic gill disease in farmed salmon since 1984 in Tasmania and later in European farming of Atlantic salmon in Ireland, UK, Faroe Islands and in particular the Western Coast of Norway. Also infecting other farmed fish species as turbot, sea bass and sea bream.

The term infestation in general relates to parasitic diseases caused by animals such as arthropods (i.e. mites, ticks, and lice) and worms, while parasitic disease caused by protozoa, fungi, bacteria, and viruses, are called infections.

Examples of *Salmonides* in which an ectoparasitic infection may be treated and/or prevented with a probiotic composition of the present document comprise the species (reproduced from FishBase under CC 3.0 license from https://www.fishbase.se/identification/specieslist.php?famcode=76): *Brachymystax lenok, Brachymystax savinovi, Brachymystax tumensis, Coregonus albellus, Coregonus albula, Coregonus alpenae, Coregonus alpinus, Coregonus anaulorum, Coregonus arenicolus, Coregonus artedi, Coregonus atterensis, Coregonus austriacus, Coregonus autumnalis, Coregonus baerii, Coregonus baicalensis, Coregonus baunti, Coregonus bavaricus, Coregonus bezola, Coregonus candidus, Coregonus chadary, Coregonus clupeaformis, Coregonus clupeoides, Coregonus confusus, Coregonus danneri, Coregonus duplex, Coregonus fatioi, Coregonus fera, Coregonus fontanae, Coregonus gutturosus, Coregonus heglingus, Coregonus hiemalis, Coregonus hoferi, Coregonus holsata, Coregonus hoyi, Coregonus huntsmani, Coregonus johannae, Coregonus kiletz, Coregonus kiyi, Coregonus ladogae, Coregonus laurettae, Coregonus lavaretus, Coregonus lucinensis, Coregonus lutokka, Coregonus macrophthalmus, Coregonus maraena, Coregonus maraenoides, Coregonus maxillaris, Coregonus megalops, Coregonus migratorius, Coregonus muksun, Coregonus nasus,*

*Coregonus nelsonii, Coregonus nigripinnis, Coregonus nilssoni, Coregonus nipigon, Coregonus nobilis, Coregonus oxyrinchus, Coregonus palaea, Coregonus pallasii, Coregonus peled, Coregonus pennantii, Coregonus pidschian, Coregonus pollan, Coregonus pravdinellus, Coregonus reighardi, Coregonus renke, Coregonus restrictus, Coregonus sardinella, Coregonus stigmaticus, Coregonus subautumnalis, Coregonus suidteri, Coregonus trybomi, Coregonus tugun, Coregonus ussuriensis, Coregonus vandesius, Coregonus vessicus, Coregonus wartmanni, Coregonus widegreni, Coregonus zenithicus, Coregonus zuerichensis, Coregonus zugensis, Hucho bleekeri, Hucho hucho, Hucho ishikawae, Hucho taimen, Oncorhynchus aguabonita, Oncorhynchus apache, Oncorhynchus chrysogaster, Oncorhynchus clarkii, Oncorhynchus formosanus, Oncorhynchus gilae, Oncorhynchus gorbuscha, Oncorhynchus iwame, Oncorhynchus kawamurae, Oncorhynchus keta, Oncorhynchus kisutch, Oncorhynchus masou, Oncorhynchus mykiss, Oncorhynchus nerka, Oncorhynchus rhodurus, Oncorhynchus tshawytscha, Parahucho perryi, Prosopium abyssicola, Prosopium coulterii, Prosopium cylindraceum, Prosopium gemmifer, Prosopium spilonotus, Prosopium williamsoni, Salmo abanticus, Salmo akairos, Salmo aphelios, Salmo balcanicus, Salmo carpio, Salmo caspius, Salmo cenerinus, Salmo cettii, Salmo chilo, Salmo ciscaucasicus, Salmo coruhensis, Salmo dentex, Salmo euphrataeus, Salmo ezenami, Salmo farioides, Salmo ferox, Salmo fibreni, Salmo ischchan, Salmo kottelati, Salmo labecula, Salmo labrax, Salmo letnica, Salmo lourosensis, Salmo lumi, Salmo macedonicus, Salmo macrostigma, Salmo marmoratus, Salmo montenigrinus, Salmo multipunctata, Salmo nigripinnis, Salmo obtusirostris, Salmo ohridanus, Salmo okumusi, Salmo opimus, Salmo pallaryi, Salmo pelagonicus, Salmo pellegrini, Salmo peristericus, Salmo platycephalus, Salmo rhodanensis, Salmo rizeensis, Salmo salar, Salmo schiefermuelleri, Salmo stomachicus, Salmo taleri, Salmo tigridis, Salmo trutta, Salmo viridis, Salmo visovacensis, Salmo zrmanjaensis, Salvelinus agassizii, Salvelinus albus, Salvelinus alpinus, Salvelinus anaktuvukensis, Salvelinus andriashevi, Salvelinus boganidae, Salvelinus colii, Salvelinus confluentus, Salvelinus curilus, Salvelinus czerskii, Salvelinus drjagini, Salvelinus elgyticus, Salvelinus evasus, Salvelinus faroensis, Salvelinus fimbriatus, Salvelinus fontinalis, Salvelinus gracillimus, Salvelinus grayi, Salvelinus gritzenkoi, Salvelinus inframundus, Salvelinus jacuticus, Salvelinus japonicus, Salvelinus killinensis, Salvelinus krogiusae, Salvelinus kronocius, Salvelinus kuznetzovi, Salvelinus lepechini, Salvelinus leucomaenis, Salvelinus levanidovi, Salvelinus lonsdalii, Salvelinus mallochi, Salvelinus malma, Salvelinus maxillaris, Salvelinus murta, Salvelinus namaycush, Salvelinus neiva, Salvelinus neocomensis, Salvelinus obtusus, Salvelinus perisii, Salvelinus profundus, Salvelinus salvelinoinsularis, Salvelinus schmidti, Salvelinus struanensis, Salvelinus taimyricus, Salvelinus taranetzi, Salvelinus thingvallensis, Salvelinus tolmachoffi, Salvelinus umbla, Salvelinus vasiljevae, Salvelinus willoughbii, Salvelinus youngeri, Salvethymus svetovidovi, Stenodus leucichthys, Stenodus nelma, Thymallus arcticus, Thymallus baicalensis, Thymallus brevipinnis, Thymallus brevirostris, Thymallus burejensis, Thymallus flavomaculatus, Thymallus grubii, Thymallus mertensii, Thymallus nigrescens, Thymallus pallasii, Thymallus svetovidovi, Thymallus thymallus, Thymallus tugarinae and Thymallus yaluensis.*

Examples of sea lice, the infestation of which may be treated and/or prevented by administration of the probiotic composition disclosed herein comprise *Lepeophtheirus acutus, Lepeophtheirus aesopus, Lepeophtheirus alvaroi, Lepeophtheirus anguilli, Lepeophtheirus appendiculatus, Lepeophtheirus argentus, Lepeophtheirus atypicus, Lepeophtheirus azoricus, Lepeophtheirus bagri, Lepeophtheirus bifidus, Lepeophtheirus bifurcatus, Lepeophtheirus bonaci, Lepeophtheirus brachyurus, Lepeophtheirus breviventris, Lepeophtheirus bychowskyi, Lepeophtheirus chaenichthyis, Lepeophtheirus chantoni, Lepeophtheirus chilensis, Lepeophtheirus clarionensis, Lepeophtheirus confusum, Lepeophtheirus constrictus, Lepeophtheirus cossyphi, Lepeophtheirus crabro, Lepeophtheirus crassus, Lepeophtheirus cuneifer, Lepeophtheirus curtus, Lepeophtheirus dissimulatus, Lepeophtheirus distinctus, Lepeophtheirus edwardsi, Lepeophtheirus elegans, Lepeophtheirus eminens, Lepeophtheirus epinepheli, Lepeophtheirus erecsoni, Lepeophtheirus etelisi, Lepeophtheirus europaensis, Lepeophtheirus exilipes, Lepeophtheirus exsculptus, Lepeophtheirus formosanus, Lepeophtheirus frecuens, Lepeophtheirus furcatus, Lepeophtheirus goniistii, Lepeophtheirus grohmanni, Lepeophtheirus gusevi, Lepeophtheirus hapalogenyos, Lepeophtheirus hastatus, Lepeophtheirus heegaardi, Lepeophtheirus hexagrammi, Lepeophtheirus hidekoi, Lepeophtheirus hippoglossi, Lepeophtheirus histiopteridi, Lepeophtheirus hospitalis, Lepeophtheirus hummi, Lepeophtheirus intercurreus, Lepeophtheirus interitus, Lepeophtheirus kabatai, Lepeophtheirus krishnai, Lepeophtheirus lagocephali, Lepeophtheirus lalandei, Lepeophtheirus lateolabraxi, Lepeophtheirus latigenitalis, Lepeophtheirus lewisi, Lepeophtheirus lichiae, Lepeophtheirus litus, Lepeophtheirus longiabdominis, Lepeophtheirus longicaudus, Lepeophtheirus longipalpus, Lepeophtheirus longipes, Lepeophtheirus longispinosus, Lepeophtheirus longiventralis, Lepeophtheirus marcepes, Lepeophtheirus marginatus, Lepeophtheirus molvae, Lepeophtheirus monacanthus, Lepeophtheirus mugiloidis, Lepeophtheirus muraenae, Lepeophtheirus nanaimoensis, Lepeophtheirus natalensis, Lepeophtheirus nordmanni, Lepeophtheirus oblitus, Lepeophtheirus palliatus, Lepeophtheirus paralichthydis, Lepeophtheirus parvicruris, Lepeophtheirus parviventris, Lepeophtheirus parvulus, Lepeophtheirus parvus, Lepeophtheirus paulus, Lepeophtheirus pectoralis, Lepeophtheirus perpes, Lepeophtheirus platensis, Lepeophtheirus plectropomi, Lepeophtheirus plotosi, Lepeophtheirus pollachius, Lepeophtheirus polyprioni, Lepeophtheirus pravipes, Lepeophtheirus quadratus, Lepeophtheirus remiopsis, Lepeophtheirus renalis, Lepeophtheirus rhinobati, Lepeophtheirus robertae, Lepeophtheirus robustus, Lepeophtheirus rotundatus, Lepeophtheirus rotundipes, Lepeophtheirus rotundiventris, Lepeophtheirus schaadti, Lepeophtheirus scutiger, Lepeophtheirus sekii, Lepeophtheirus selkirki, Lepeophtheirus semicossyphi, Lepeophtheirus sheni, Lepeophtheirus shiinoi, Lepeophtheirus sigani, Lepeophtheirus simplex, Lepeophtheirus spatha, Lepeophtheirus spinifer, Lepeophtheirus sturionis, Lepeophtheirus suhmi, Lepeophtheirus tamladus, Lepeophtheirus tenuis, Lepeophtheirus thompsoni, Lepeophtheirus tuberculatus, Lepeophtheirus uluus, Lepeophtheirus unispinosus, Lepeophtheirus yanezi, Lepeophtheirus zbigniewi, Caligus abigailae, Caligus absens, Caligus acanthopagri, Caligus adanensis, Caligus aduncus, Caligus affinis, Caligus afurcatus, Caligus alaihi, Caligus alepicolus, Caligus amblygenitalis, Caligus antennatus, Caligus apodus, Caligus arii, Caligus ariicolus, Caligus asperimanus, Caligus asymmetricus, Caligus atromaculatus, Caligus balistae, Caligus belones, Caligus berychis, Caligus biaculeatus, Caligus bicycletus, Caligus bifurcus, Caligus biseriodentatus, Caligus bocki, Caligus bonito, Caligus brevicaudatus, Caligus brevicaudus, Caligus brevipedis, Caligus brevis, Caligus buechlerae,*

Caligus callaoensis, Caligus callyodoni, Caligus calotomi, Caligus carangis, Caligus centrodonti, Caligus chamelensis, Caligus cheilodactyli, Caligus chelifer, Caligus chiastos, Caligus chorinemi, Caligus chrysophrysi, Caligus clavatus, Caligus clemensi, Caligus confusus, Caligus constrictus, Caligus cookeoli, Caligus cordiventris, Caligus cordyla, Caligus cornutus, Caligus coryphaenae, Caligus costatus, Caligus cresseyorum, Caligus crusmae, Caligus curtus, Caligus cybii, Caligus dactylopteni, Caligus dakari, Caligus dampieri, Caligus dasyaticus, Caligus debueni, Caligus deformis, Caligus diaphanus, Caligus dicentrarchi, Caligus dieuzeidei, Caligus digitatus, Caligus dubius, Caligus elasmobranchi, Caligus eleutheronemi, Caligus elongatus, Caligus engraulidis, Caligus enormis, Caligus epidemicus, Caligus epinepheli, Caligus equulae, Caligus evelynae, Caligus eventilis, Caligus fajerae, Caligus fistulariae, Caligus flexispina, Caligus fortis, Caligus fronsuganinus, Caligus fugu, Caligus furcisetifer, Caligus glacialis, Caligus glandifer, Caligus grandiabdominalis, Caligus guerini, Caligus gurnardi, Caligus haemulonis, Caligus hamatus, Caligus hamruri, Caligus hemiconiati, Caligus hobsoni, Caligus hoplognathi, Caligus hottentotus, Caligus hyalinae, Caligus hyalinus, Caligus hyporhamphi, Caligus ignotus, Caligus ilhoikimi, Caligus inanis, Caligus infestans, Caligus inopinatus, Caligus irritans, Caligus isonyx, Caligus itacurussensis, Caligus jawahari, Caligus kabatae, Caligus kahawai, Caligus kala, Caligus kalumai, Caligus kanagurta, Caligus kapuhili, Caligus keralensis, Caligus kirti, Caligus klawei, Caligus kurochkini, Caligus kuwaitensis, Caligus labracis, Caligus lacustris, Caligus lagocephali, Caligus lalandei, Caligus laminatus, Caligus laticaudus, Caligus latigenitalis, Caligus latus, Caligus lessonius, Caligus lethrinicola, Caligus lichiae, Caligus ligatus, Caligus ligusticus, Caligus lini, Caligus littoralis, Caligus lobodes, Caligus lolligunculae, Caligus longiabdominis, Caligus longicaudatus, Caligus longicaudus, Caligus longipedis, Caligus longipes, Caligus longiramus, Caligus longirostris, Caligus longispinosus, Caligus lunatus, Caligus lutjani, Caligus macarovi, Caligus macoloricola, Caligus macrurus, Caligus malabaricus, Caligus mebachii, Caligus minimus, Caligus mordax, Caligus mortis, Caligus mugilis, Caligus mulli, Caligus musaicus, Caligus mutabilis, Caligus nanhaiensis, Caligus nataliae, Caligus nengai, Caligus neoaricolus, Caligus nibeae, Caligus nolani, Caligus novocaledonicus, Caligus nuenonnae, Caligus oculicola, Caligus ocyurus, Caligus ogawai, Caligus olsoni, Caligus omissus, Caligus orientalis, Caligus oviceps, Caligus pagelli, Caligus pageti, Caligus pagri, Caligus pagrosomi, Caligus pampi, Caligus paranengai, Caligus parapetalopsis, Caligus parvilatus, Caligus patulus, Caligus pauliani, Caligus pectinatus, Caligus pelagicus, Caligus pelamydis, Caligus penrithi, Caligus pharaonis, Caligus phipsoni, Caligus placidus, Caligus planktonis, Caligus platurus, Caligus platytarsis, Caligus polycanthi, Caligus pomacentrus, Caligus pomadasi, Caligus praecinctorius, Caligus praetextus, Caligus priacanthi, Caligus productus, Caligus pseudokalumai, Caligus pseudoproductus, Caligus pseudorhombi, Caligus pterois, Caligus punctatus, Caligus quadratus, Caligus quadrigenitalis, Caligus randalli, Caligus raniceps, Caligus rapax, Caligus regalis, Caligus reniformis, Caligus robustus, Caligus rogercresseyi, Caligus rotundigenitalis, Caligus rufimaculatus, Caligus saucius, Caligus savala, Caligus schistonyx, Caligus schlegeli, Caligus sciaenops, Caligus sclerotinosus, Caligus scribae, Caligus sensorius, Caligus sepetibensis, Caligus seriolae, Caligus seriolicolus, Caligus serratus, Caligus sibogae, Caligus sicarius, Caligus similis, Caligus solea, Caligus spinosus, Caligus stocki, Caligus stokesi, Caligus stromatei, Caligus subparvus, Caligus suffuscus, Caligus tanago, Caligus temnodontis, Caligus tenax, Caligus tenuicauda, Caligus tenuifurcatus, Caligus tenuis, Caligus tenuis, Caligus teres, Caligus tetrodontis, Caligus thyrsitae, Caligus torpedinis, Caligus trachynoti, Caligus triabdominalis, Caligus triangularis, Caligus tripedalis, Caligus truttae, Caligus turbidus, Caligus tylosuri, Caligus undulatus, Caligus uniartus, Caligus upenei, Caligus ventrosetosus, Caligus vexator, Caligus willungae, Caligus wilsoni, Caligus xystercus, Caligus zei, Caligus zylanica.

A "culture" includes all forms of bacterial culture, both in broth, on agar and in any other media. A "single culture" refers to a culture containing only one bacterial strain, i.e. a pure culture. A "mixed culture" refers to a culture wherein two or more bacterial strains, species and/or general are grown together or wherein two or more bacterial strains, species and/or genera are grown separately and thereafter mixed.

"CFU" stands for "colony forming units" which is a unit used for estimating the number of viable bacterial cells in a sample.

"dpi" is an abbreviation for "days post infection", the number of days after the fish were infected with ectoparasites.

Milliliter is herein abbreviated with "ml" or "mL".

"Stembiont" is a registered trademark for a probiotic composition comprising bacteria of the Aliivibrio njordis and/or Aliivibrio balderis and/or Aliivibrio nannie species.

DETAILED DESCRIPTION

Figure 1:
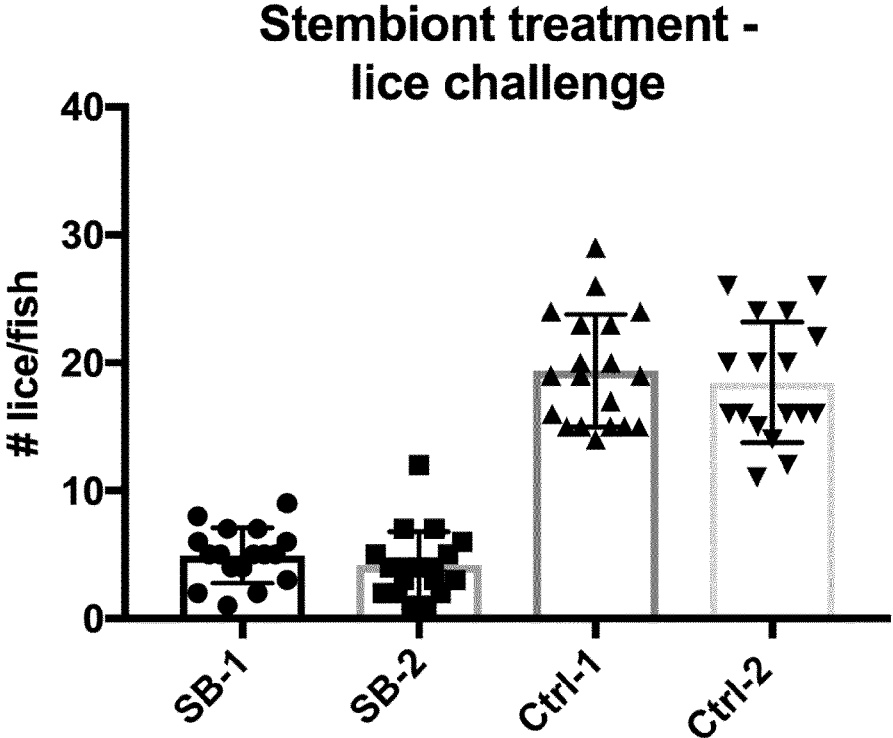
FIG. 1: Probiotic application treatment ("Stembiont") followed by lice challenge according to Example 1.

The present document is directed to treating and/or preventing ectoparasitic infestations and/or gill parasite infections in teleosts. The present inventors surprisingly found that by administering probiotic bacteria to the teleosts, infestations of ectoparasites and/or gill parasite infections could be prevented and/or treated.

The present document is thus directed to a probiotic composition comprising probiotic bacteria of one or both of the species Aliivibrio njordis and/or Aliivibrio balderis for use in the treatment and/or prevention of an ectoparasitic infestation and/or gill parasite infection in a teleost. The present document is also directed to the use of probiotic bacteria of one or both of the species Aliivibrio njordis and Aliivibrio balderis for the preparation of a medicament in the form of a probiotic composition as disclosed for the treatment and/or prevention of an ectoparasitic infestation and/or gill parasite infection in a teleost. The present document is further directed to a method for treating and/or preventing an ectoparasitic infestation and/or gill parasite infection in a teleost, said method comprising administering a probiotic composition comprising probiotic bacteria of one or both of the species *Aliivibrio* njordis and *Aliivibrio* balderis to a teleost in need thereof. The probiotic composition, its preparation and administration will be further described in the below.

Preferably, the composition comprises both of the *Aliivibrio* njordis and *Aliivibrio* balderis species. A probiotic composition of the present document may also comprise one or more of a probiotic bacterium of the species *Aliivibrio* nannie, *Psychrobacter* piscimesodermis, *Psychrobacter* piscimesenchymalis, *Psychrobacter* piscisubcutanea, *Pseudomonas* salmosubcutaneae, *Pseudomonas* salmosubpectoralis and/or *Pseudomonas* salmointermuscularis. It is also possible to provide the probiotic bacteria in separate probiotic compositions which then are administered, simultaneously or sequentially, to a teleost. The same is true for the other probiotic bacterial species mentioned herein to be useful for the purpose of treating and/or preventing an ectoparasitic infestation and/or gill parasite infection in a teleost, i.e. the probiotic bacteria can be provided in the same probiotic composition or in one or more separate probiotic compositions, each comprising one or more probiotic bacterial species and/or strains. Thus, unless otherwise stated, the term "probiotic composition for use in the treatment and/or prevention of an ectoparasitic infestation and/or gill parasite infection", and the like, refers to either a single probiotic composition comprising one or more probiotic bacterial species and/or strains or two or more probiotic compositions, each comprising one or more probiotic bacterial species and/or strains intended to be administered simultaneously or sequentially to a teleost. Likewise, the term "probiotic composition" as used herein refers to either a single probiotic composition comprising one or more probiotic bacterial species and/or strains of two or more probiotic compositions, each comprising one or more probiotic bacterial species and/or strains intended to be administered simultaneously or sequentially to a teleost.

The probiotic bacteria of composition of the present document may consist of *Aliivibrio* njordis and/or *Aliivibrio* balderis and optionally one or more of a bacterial species selected from the group consisting *Aliivibrio* nannie, *Psychrobacter* piscimesodermis, *Psychrobacter* piscimesenchymalis, *Psychrobacter* piscisubcutanea, *Pseudomonas* salmosubcutaneae, *Pseudomonas* salmosubpectoralis and *Pseudomonas* salmointermuscularis.

Thus, the present document also discloses a probiotic composition comprising probiotic bacteria of the species *Aliivibrio* njordis and/or *Aliivibrio* balderis, and optionally *Aliivibrio* nannie for use in the treatment and/or prevention of an ectoparasitic infestation and/or gill parasite infection in a teleost, wherein said probiotic composition is administered to said teleost before, during or after administration of one or more further probiotic composition(s) comprising one or more of a probiotic bacterium selected from the group consisting of bacteria of the species *Psychrobacter* piscimesodermis, *Psychrobacter* piscimesenchymalis, *Psychrobacter* piscisubcutanea, *Pseudomonas* salmosubcutaneae, *Pseudomonas* salmosubpectoralis and/or *Pseudomonas* salmointermuscularis.

The present document also discloses the use of a a probiotic composition comprising probiotic bacteria of the species *Aliivibrio* njordis and/or *Aliivibrio* balderis, and optionally *Aliivibrio* nannie and a probiotic composition comprising one or more of a probiotic bacterium selected from the group consisting of bacteria of the species *Psy-*

*chrobacter* piscimesodermis, *Psychrobacter* piscimesenchymalis, *Psychrobacter* piscisubcutanea, *Pseudomonas* salmosubcutaneae, *Pseudomonas* salmosubpectoralis and/or *Pseudomonas* salmointermuscularis for the preparation of a medicament in the form of a probiotic composition for the treatment and/or prevention of an ectoparasitic infestation or gill parasite infection in a teleost, wherein said probiotic composition *Aliivibrio* njordis and/or *Aliivibrio* balderis, and optionally *Aliivibrio* nannie is administered before, during or after administration of the one or more further probiotic composition(s) comprising a probiotic bacterium selected from the group consisting of bacteria of the species *Psychrobacter* piscimesodermis, *Psychrobacter* piscimesenchymalis, *Psychrobacter* piscisubcutanea, *Pseudomonas* salmosubcutaneae, *Pseudomonas* salmosubpectoralis and/or *Pseudomonas* salmointermuscularis.

The present document further discloses a method for treating and/or preventing an ectoparasitic infestation and/or gill parasite infection in a teleost wherein said method comprises administering a therapeutically effective amount of a probiotic composition comprising a probiotic bacterium of the species *Aliivibrio* njordis and/or *Aliivibrio* balderis, and optionally *Aliivibrio* nannie, before, during or after administration of a therapeutically effective amount of one or more further probiotic composition(s) comprising one or more of a probiotic bacterium selected from the group consisting of bacteria of the species *Psychrobacter* piscimesodermis, *Psychrobacter* piscimesenchymalis, *Psychrobacter* piscisubcutanea, *Pseudomonas* salmosubcutaneae, *Pseudomonas* salmosubpectoralis and/or *Pseudomonas* salmointermuscularis.

It is also possible to use two or more different strains of a probiotic bacterial species in the probiotic composition and/or probiotic bacteria of the same bacterial species/strain but grown under different growth conditions.

The probiotic composition is administered to teleosts in order to treat and/or prevent an ectoparasitic infestation.

The teleost may be any kind of teleost, such as a teleost living in marine environments (salt or brackish water) or a teleost living in fresh water. Some teleosts, like teleosts of the family Salmonidae live in both fresh and salt water depending on where in their life cycle they are. Some teleosts, such as wrasse (Labridae) feed on ectoparasites of other teleosts.

Examples of teleosts which can benefit from a treatment with the probiotic composition disclosed herein are teleosts of the family Salmonidae, such as salmon, trout, and chars. Examples of species of the family Salmonidae are Atlantic salmon (*Salmo salar*), brown trout (sea trout: *Salmo trutta*), Arctic char (*Salvelinus alpinus*), and/or any species of Pacific salmon, such as Coho (Silver) salmon (*Oncorhynchus kisutch*), Chinook (King) (*Oncorhynchus tshawytscha*), pink (Humpy) salmon (*Oncorhynchus gorbuscha*), chum (Dog) salmon (*Oncorhynchus keta*), sockeye (*Oncorhynchus nerka*), cutthroat (*Oncorhynchus clarki clarki*) and steelhead (rainbow trout) (*Oncorhynchus mykiss*).

Further examples of marine teleosts are turbot, sea bass and sea bream. Other examples are Atlantic cod, cleaner fish like lump fish and wrasses and freshwater fish as carps and perch.

Without wishing to be bound by theory, one effect of the probiotic bacteria in the probiotic composition of the present document may be that they change the goblet cells of the teleosts so that these respond more efficiently, rapidly and/or with a higher response to an irritation from ectoparasites trying to attach to the skin or surface of the teleost with an increased flow of mucus, which prevents the ectoparasites from attaching. The ectoparasite, the infection of which is to be treated and/or prevented, may thus be any ectoparasite.

One example of an ectoparasite infestation which may be treated and/or prevented by the administration of a composition according to the present document is a sea lice infestation. The sea lice may e.g. be of the genera *Lepeophtheirus*, such as of the species *L. salmonis*, and/or *Caligus*, such as of the species *C. rogercresseyi* and/or *C. elongatus*.

A disease caused by an ectoparasite may also be caused by an infestation by an ectoparasite of the genus *Gyrodactylus*, such as *Gyrodactylus salaris*, an ectoparasite of the genus Cryptocaryon, such as Cryptocaryon *irritans*, an ectoparasite of the genus *Lernaeocera*, such as *Lernaeocera branchialis*, an ectoparasite of the genus *Pseudorhabdosynochus*, and/or an ectoparasite of the genus Amyloodinium.

Examples of parasites causing gill infections are amoebas, such as an amoeba of the genus Neoparamoeba, such as Neoparamoeba perurans, The probiotic bacteria may be administered separately or in any combination of two or more of the species and/or different strains of the different species. Bacteria of the different species and/or different strains may be used at any relative ratio. However, typically, the ratio is about 1:10 to about 10:1 between any two species/strains when the bacteria are used in combination. For example, the ratio between any two species/strains when the bacteria are used in combination may be 1:4 to 4:1, 1:3 to 3:1, 1:2 to 2:1 or 1:1. However, it may also be about 1:100 to 100:1.

Probiotic bacteria of the different species disclosed herein and/or different strains within the same species may be mixed before administration. The different species of probiotic bacteria and/or different strains within the same species may also be cultured together in the same culture. It is also possible to culture two or more strains of the same species together or in combination with one or more strains of another species.

Probiotic bacteria of the different species and/or different strains within the same species may be administered separately but simultaneously to the same population of teleosts. It is also possible to expose the teleost to probiotic bacteria of the different species disclosed herein and/or strains of one or more of the species sequentially by administering one or more probiotic bacterial species/strains before the addition of one or more further probiotic bacterial species/strains. If such a sequential administration of the probiotic bacteria is to be used, it is possible to add the bacteria sequentially but without removing previously added bacteria or to effect removal of previously added bacteria before new bacteria are added, e.g. by exchanging the volume of bacteria containing water for new water before addition of further bacteria.

Bacterial Species and Strains

The probiotic bacteria used in accordance with the present document are of the *Aliivibrio* njordis and/or *Aliivibrio* balderis species. Further, bacteria of the species *Aliivibrio* nannie may be used.

In addition to the above mentioned *Aliivibrio* species, probiotic bacteria of the species *Psychrobacter* piscimesodermis, *Psychrobacter* piscimesenchymalis, *Psychrobacter* piscisubcutanea, *Pseudomonas* salmosubcutaneae, *Pseudomonas* salmosubpectoralis and/or *Pseudomonas* salmointermuscularis may be used.

As mentioned above, the probiotic composition disclosed herein comprises probiotic bacteria of the species *Aliivibrio* njordis and/or *Aliivibrio* balderis. *Aliivibrio* njordis may for example be *Aliivibrio* njordis strain B1-25, 18-1/2013 mandib V11, which has been deposited at National Collection of Industrial and Marine Bacteria and has been assigned accession number NCIMB 42593. *Aliivibrio* balderis may for example be *Aliivibrio* balderis B1-24, 18-1/2013 kidn V12, which has been deposited at National Collection of Industrial and Marine Bacteria and has been assigned accession number NCIMB 42592.

One exemplary strain of *Aliivibrio* nannie is *Aliivibrio* nannie B8-24, 313/2013 kidn V13, which has been deposited at National Collection of Industrial and Marine Bacteria and has been assigned accession number NCIMB 42594.

These exemplary strains of A. njordis, A. balderis and A. nannie, respectively, have been isolated in Norway and deposited according to the Budapest Treaty on Jun. 17, 2016, at the National Collection of Industrial and Marine Bacteria (Ferguson Building, Craibstone Estate, Bucksburn, Aberdeen, AB21 9YA, Scotland, United Kingdom). Further details on the isolation and growth of these *Aliivibrio* strains are given in WO 2018/007632.

*Psychrobacter* piscimesodermis may for example be *Psychrobacter* piscimesodermis Fisk 1, 41, 6/3-2014 Atl. Salm, which has been deposited at National Collection of Industrial and Marine Bacteria and has been assigned accession number NCIMB 42947. *Psychrobacter* piscimesenchymalis may for example be *Psychrobacter* piscimesenchymalis Fisk 2, 42, 6/3-2014 Atl. salm, which has been deposited at National Collection of Industrial and Marine Bacteria and has been assigned accession number NCIMB 42948. *Psychrobacter* piscisubcutanea may for example be *Psychrobacter* piscisubcutanea Fisk 3, 43, 6/3-2014 Atl. Salm, which has been deposited at National Collection of Industrial and Marine Bacteria and has been assigned accession number NCIMB 42949.

These exemplary species of *Psychrobacter* have been isolated in Norway and deposited according to the Budapest Treaty on Jan. 4, 2018, at the National Collection of Industrial and Marine Bacteria (Ferguson Building, Craibstone Estate, Bucksburn, Aberdeen, AB21 9YA, Scotland, United Kingdom). Further details on the isolation and growth of these *Psychrobacter* strains are given in WO 2019/135009.

*Pseudomonas* salmosubcutaneae may for example be *Pseudomonas* salmosubcutaneae Fisk 3, 13/5-2014, hb, Atl. Salm., which has been deposited at National Collection of Industrial and Marine Bacteria and has been assigned accession number NCIMB 43330. *Pseudomonas* salmosubpectoralis may for example be *Pseudomonas* salmosubpectoralis Fisk 3, 13/5-2014, ba, Atl. salm., which has been deposited at National Collection of Industrial and Marine Bacteria and has been assigned accession number NCIMB 43331. *Pseudomonas* salmointermuscularis may for example be *Pseudomonas* salmointermuscularis Fisk 4, 13/5-2014, ha, Atl. salm., which has been deposited at National Collection of Industrial and Marine Bacteria and has been assigned accession number NCIMB 43332.

These three exemplary species of *Pseudomonas* have been isolated in Norway and deposited according to the Budapest Treaty on Dec. 20, 2018, at the National Collection of Industrial and Marine Bacteria (Ferguson Building, Craibstone Estate, Bucksburn, Aberdeen, AB21 15 9YA, Scotland, United Kingdom). Further details on the isolation and growth of these *Pseudomonas* strains are given in WO 2019/135009.

Preparation of the Probiotic Bacterial Composition

The probiotic composition comprising *Aliivibrio* njordis and/or *Aliivibrio* balderis and optionally additional bacterial species as described elsewhere herein may be prepared by culturing the different bacterial species and/or strains of the same bacterial species together. It is also possible to grow the different bacterial species and/or strains in separate cultures and mix them before administration to a teleost. Also, it is possible to grow the bacteria separately and administer them to a teleost without prior mixing, such by simultaneous or consecutive administration. Further, it is possible to grow two or more different bacterial species and/or strains of the same bacterial species together and mix with one or more culture(s) of one or more bacterial species and/or strains or to administer such cultures separately (simultaneously or consecutively) to a teleost.

The probiotic bacteria may be used together with their used growth medium, i.e. the probiotic composition comprises the used growth medium. One advantage with this is that beneficial substances that are produced by the probiotic bacteria will be present in the probiotic composition. Alternatively, the probiotic bacteria may be separated from the used growth medium (e.g. by centrifugation or filtration) and resuspended in another medium, such as new growth medium, a buffer (such as phosphate buffered saline, PBS) or a salt solution (such as a sodium salt solution). In this case, the probiotic bacteria may be washed one or more times with e.g. growth medium, a buffer, such as PBS or saline (such as a sodium salt solution).

The concentration of the probiotic bacteria in the probiotic composition may vary but is typically in the range of from $10^2$ to $10^{14}$ CFU per mi, such as from $10^8$ to $10^{13}$, $10^9$ to $10^{13}$, $10^{10}$ to $10^{12}$, $10^2$ to $10^7$, or from $10^5$ to $10^7$ CFU per ml.

The ratio of the different probiotic bacterial species in the probiotic composition may vary depending on e.g. whether the bacteria are grown together or separately and mixed before or upon administration. Typically *Aliivibrio* njordis and/or Allivibrio balderis are present in a ratio of about 1:10 to 10:1, such as about a ratio of 3:10 to 10:3 or a ratio of about 1:1. When the probiotic composition further comprises bacteria of the species A. nannie, each bacterial species is typically constitutes about 33% of the number of probiotic bacteria in the composition.

In addition to the probiotic bacteria, the probiotic composition may comprise e.g. a pharmaceutically acceptable excipient and/or adjuvant.

It is also possible to add a chemical parasitic infestation treatment agent, such as an organophosphate, a carbamate, a pyrethroid, a pyrethrin, a synergist, an insect growth regulating chemical and/or an avermectin to the probiotic composition comprising probiotic bacteria described herein and/or to the further probiotic composition described herein. Thus, the probiotic composition described herein and/or the further probiotic composition described herein may comprise a chemical parasitic infestation treatment agent such as those mentioned above. Additionally or alternatively, it is possible to administer such a chemical parasitic infection treatment agent in conjunction with the administration of the probiotic composition, such as simultaneously or sequentially with the administration of the probiotic composition.

It will be appreciated that the probiotic composition described herein may be provided as a kit of parts. For instance, there is provided a kit of parts comprising:

(i) a probiotic composition as described herein, and (ii) one or more further probiotic composition(s) as described herein, and/or (iii) instructions for use.

It will be appreciated that the instructions for use described herein may describe that the probiotic composition described herein should be administered before, during and/or after administration of the one or more further probiotic composition(s) as described herein. The administration may intend administration to teleosts.

Administration of the Probiotic Bacteria to Teleosts

The probiotic composition may e.g. be administered to teleosts via bath or dip administration in salt, fresh or brackish water, by oral administration or by injection, such as by intraperitoneal administration, intramuscular administration, or subcutaneous administration.

When the probiotic composition is administered via bath or dip administration, the probiotic bacteria are cultured in a suitable manner and then added to water. The water to which the bacteria are added may be the water that the fish are already contained in or may be water in another tank, cage or the like to which the fish are transferred. The water is typically the same kind of water that the fish are contained in depending on their growth stage. For e.g. salmon at the post smolt stage, the water is typically natural sea water. However, it is also possible to transfer the fish to another kind of water during the treatment. For example, salmon at the pre-smolt stage, which live in fresh water, may be transferred to salt water, such as natural seawater, during the exposure to the probiotic bacteria and then moved back to the fresh water. The water to which the bacteria are added typically has a salinity of about 0.5 to about 4 weight %, such as about 0.9 to about 4 weight %, such as about 2 to 4 weight %, although the water may also be fresh water which has a much lower salinity. It is thus possible to use already propagated live cells to bath fish at lower salt concentrations down to fresh water at typical shorter time intervals not killing the probiotic bacteria.

The teleosts are exposed to the bathing water containing the probiotic bacteria for a time sufficient for enough bacteria to be administered to the teleosts to obtain the desired effects. This time will depend on e.g. the concentration of probiotic bacteria in the probiotic composition used, the type and status of the teleosts that are to be exposed etc. Typically, an exposure time of a few seconds (dip administration) to a couple of hours may be used, such as from about 1 second to about 5 hours, such as from about 1 second to about 2 hours, such as from about 1 second to about 1 hour, such as from about 30 seconds to about 1 hour or from about 1 minute to about 30 minutes. Increasing the concentration of probiotic bacteria in the water will generally decrease the exposure time needed.

The teleosts may be exposed to the probiotic bacteria a single time or the exposure may be repeated one or more times with different time intervals. It may be beneficial to administer the probiotic composition to the teleosts at least 10 days, such as at least 15 days, 20 days, 25 days, 30 days, or 40 days, before exposure of the teleost to the ectoparasite.

The probiotic bacteria may be administered to teleosts in a therapeutically effective amount. It will be appreciated that this amount will depend on the administration route used.

Typically, when dip or bath administration is used, the concentration of the probiotic bacteria in the bath is from about $10^4$ to about $10^{13}$ CFU/ml. The concentration when using dip administration generally has to be higher than if bath administration is used, due to the shorter exposure time when dip administration is used. For dip administration, the concentration is typically from about $10^7$ to about $10^{13}$ CFU/ml, such as from about $10^7$ to about $10^{12}$ CFU/ml, such as from about $10^9$ to about $10^{12}$ CFU/ml. When applying a bath for a short single treatment interval, such as a bathing lasting for about 15 to 60 minutes, a concentration of from about$10^5$ to about $10^7$ may be suitable. For bath administration, the concentration is typically from about $10^6$ to about $10^{11}$ CFU/ml. Bacterial cultures prepared in fermenters may have a concentration of ca $10^{13}$ CFU/ml. A dilution of such a fermented culture of ca 1:100 to 1:600 may be suitable for application by bathing and a dilution of ca 1:20 for application by dipping. Adding probiotic bacteria at repeated intervals at lower concentrations down to the natural level in seawater may be beneficial to the bathed teleosts. A continuous infusion of probiotic bacteria at lower levels of concentration down to one cell/ml water may be beneficial to the teleosts.

Similarly the uptake of probiotic bacteria can be facilitated by injection of the bacteria, such as via injecting them through the abdominal wall exposing the serous linings of the peritoneal cavity to the probiotic bacteria. The concentration of bacteria used for such administration is typically from about $1 \times 10^5$ to about $1 \times 10^7$ CFU/ml, such as about $1 \times 10^6$ CFU/ml. Typically about 0.1 ml is administered per teleost giving a dose of from about $1 \times 10^4$ to about $1 \times 10^6$ CFU, such as about $1 \times 10^5$ CFU.

An additional way of administering probiotic bacteria is through oral intubation. It is considered that the immune cells in the distal part of the intestine are high in numbers and are able to transport bacteria across the intestinal wall. The concentration of bacteria in the probiotic composition used for such administration is typically from about $1 \times 10^6$ to about $1 \times 10^8$ CFU/ml, such as about $1 \times 10^7$ CFU/ml. Typically about 0.1-0.2 ml of the probiotic composition is administered. Similarly intubation of the teleost through the mouth into the stomach is tested as an effective way of administering probiotic bacteria.

Administering probiotic bacteria to spawned eggs is an important and effective way of administering probiotic bacteria. Uptake of bacteria into the eggs and adhesion to the egg shells are mechanisms that are important in the protection of the eggs and early fry. Egg yolk fry and start-feeding fry is a group of fish that also very effectively can be protected by exposing to probiotic bacteria by bathing or dipping.

It is also possible to administer the probiotic bacteria in freeze-dried form.

Administration of Probiotic Bacteria to RAS Facilities

Recirculation of water in fish farming facilities (RAS facilities) has increased due to different pressing reasons. The consumption of intake water to a farming facility can be down to only 5% of a flow-through facility. This makes it easier to construct larger and more effective facilities independent of limitations of large water supplies. The low level of intake water also reduces the risk of attracting diseases through the external water sources. On the other side there is a large risk that "house strains" of bacteria may establish in the RAS facility through the bio-filter microbiota or through the biofilms established in the tanks and pipe systems.

RAS-facilities make it possible to keep a higher temperature in the RAS water which increases the speed of the growth of salmonids.

During and after the smoltification process marine water is commonly used to some extent to warm up the water or to increase the growth towards the sea transfer. If the level of marine water can be reduced in RAS the risk of getting marine pathogens into the facility can be reduced. Typically intake of marine water is made from depths that are below the salmon sea lice zone of the marine ecosystem both in RAS plants and in flow-through plants using marine water in particular in the post smolt period to reduce the time of farming in the open net cages in the sea. Even full-scale RAS systems for farming of Atlantic salmon from egg to slaughter in RAS facilities are now constructed.

The microbiotas of the various RAS facilities are studied so far to a low extent but it seems that ulcer and fin rot and depressed growth can be substantial problems in some facilities even to an extent that the whole system is stopped, sanitized and restarted. Direct use of probiotic bacteria in RAS systems can be effective ways of securing and increasing growth and reducing disease and mortality. The bio-filter is a complex organism with dominating groups of bacteria degrading organic material from the fish coming from feces and uneaten feed. The sedimentation unit will only sediment the larger particles. In addition to the microbiota in the bio-filter degrading organic compounds and binding nutrients there is a specific microbiota related to the health and welfare of the fish. This part of the microbiota in the bio-filter is only a minor part of the total microbiota in the bio-filter and also in the water of the fish tanks. Some RAS-facilities disinfect the water coming from the bio-filter before it enters the fish tanks. This may be an important factor controlling the risk of getting infectious diseases in the populations of fish. On the other hand such disinfection may also reduce the level of naturally probiotic bacteria in the plant.

Depending on the design of the various RAS-facilities, regardless whether they use fresh or marine water, the level of the normal probiotic bacteria in the water of the facility can be low or high. To be able to secure a stable high growth with healthy fish in RAS-systems it will be optimal to add probiotic bacteria either for fresh, brackish or salt water. If fish are bathed or supplied with probiotic bacteria they will shed bacteria into the water and in that way seed the water for uptake in fish later when the water return to the fish tanks. This means that using probiotic bacteria directly to the fish will also impact the bio-filter unit and then benefit the fish after the microbial processing of the water in the bio-filter.

Application of probiotic culture may be performed any place in the cycle of RAS-facilities in addition to be directed immediately to the fish, i.e. in the fish tank water, in the bio-filter unit, after the bio-filter unit and if a disinfection step is used after the bio-filter processing of the water after the disinfection but before the water reaches the fish tanks.

In summary probiotic bacteria can be administered in a large number of different ways depending on the design and management including stage of production of each facility.

If bacteria of more than one species and/or strain are to be used, the bacteria may be grown separately (i.e. in single cultures) or in the same culture (i.e. in mixed cultures). If grown separately, bacteria of the different cultures may be mixed before addition to the water or the bacteria of the different cultures may be added separately. Probiotic bacteria obtained from different cultures (independently of whether single or mixed cultures) may also be added separately but to the same volume of water for the fish to be exposed to the different bacteria simultaneously.

Administration is preferably to be performed before infection but may also be possible during ongoing infection.

The invention will be further described in the following examples, which do not limit the scope of the invention described in the claims Experimental Section In all examples below the *Aliivibrio* njordis bacteria were of the strain *Aliivibrio* njordis strain B1-25, 18-1/2013 mandib V11, the *Aliivibrio* balderis bacteria were of the strain *Aliivibrio* balderis B1-24, 18-1/2013 kidn V12, and the *Aliivibrio* nannie bacteria were of the strain *Aliivibrio* nannie B8-24, 313/2013 kidn V13.

Example 1

Alteration of skin and potential utility of microbiome intervention in ectoparasite infestation avoidance was demonstrated by using probiotic application as a skin enhancing treatment in a laboratory study.

Two parallel groups of salmon, SB1 and SB2, consisting of 21-22 fish per group were exposed to the probiotic solution by immersing the fish in a solution comprising probiotic bacteria ("Stembiont") for 60 seconds. The probiotic composition used was a bacterial composition comprising a mixed culture of *Aliivibrio* balderis and *Aliivibrio* njordis grown together (total concentration about $1.9 \times 10^8$ cfu per ml of which about 70% was A. njordis and about 30% was A. balderis) cultured in Luria-Bertani broth (LB, 1% Bacto-tryptone, 0.5% Bacto-yeast extract and 2.5% NaCl). The probiotic composition was used at a 1/20 dilution, i.e. the concentration of bacteria in the probiotic bath was 1/20 of the concentration of the stock culture. The culture was made by mixing the two cultures of the two bacterial species after making pure cultures in LB from frozen stock cultures before mixing the cultures before the final up-scaling of the culture volumes. The cultures can also be grown separately and mixed at the time of use. The probiotic bacterial cultures were used directly without removing the broth medium.

*nis* as a challenge. A. njordis constituted about 70% and A. balderis about 30% of the bacteria in the probiotic composition.

Figure 2:
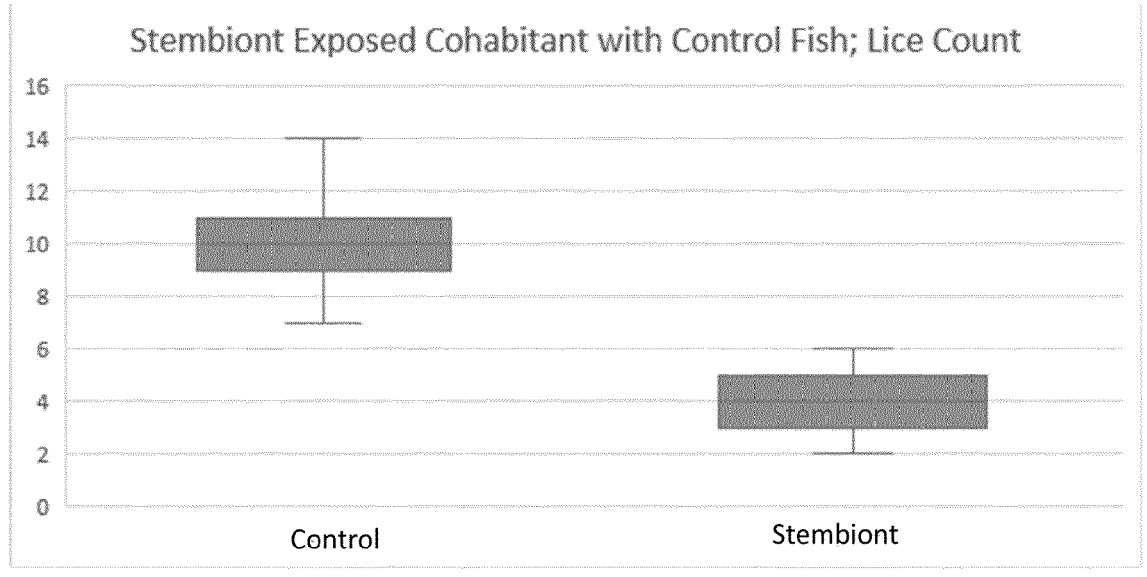
FIG. 2: Results of cohabitant fish exposed to a probiotic composition ("Stembiont") and control fish according to Example 2.

Two groups of fish treated with the probiotic composition were pit-tagged with 12 mm RFID, itag 162 under Benzoak Vet. anesthesia. Pit tags were ISO 11784 and 11785 approved, and IEC 8-2-6/29 tested. Pit tags were used as recommended from dealer, BTS-IDand were injected with a N125 needle. Fish size was >45 g and >15 cm. In one part of the study, pit tagged salmon immersed in probiotic bacteria cohabitated in the same tank with control groups not exposed to the probiotic composition. The experiment was run in duplicate tanks with 10 treated+7 untreated fish in Tank 1, and 9 treated+7 untreated fish in Tank 2 (see Table 1 and FIG. 2). This part of the study compared treatment efficacy in a co-habitant housing with ectoparasite treatments for passive immunity and vaccination.

Figure 3:
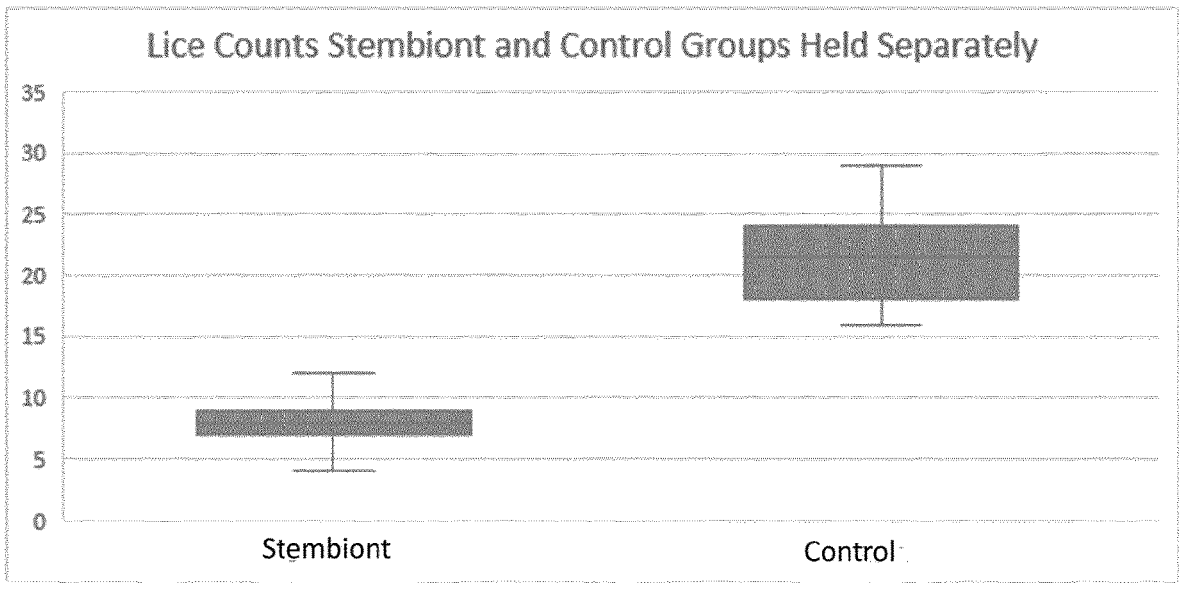
FIG. 3: Results of non-cohabitant exposed to a probiotic composition ("Stembiont") and control fish according to Example 2.

In a second part of the study, the treated and untreated fish were kept in individual tanks; two tanks with treated fish and three tanks with untreated (control) fish (see Table 2, and FIG. 3).

Fish (mean weight 150 g) were challenged with 30 lice copepodids/fish in all tanks for 30 minutes with oxygenation on Jul. 24, 2019 and assessed for lice counts on Aug. 27, 2019, i.e. 34 days after the lice were introduced.

Table 1 shows Lice counts per cohabitant tank and per group and relative percent protection (RPP) 5.5 months after exposure to the probiotic composition.

TABLE 1

| Application, Tank # | # Fish | 32 day lice count (Mean attached lice after introduction of 30 copepodids/fish) | Lice count pr fish avg all counts per appl. | RPP* of probiotic treatment within tank | RPP probiotic application |
|---|---|---|---|---|---|
| Control, 1 | 7 | 10.4 | 10.1 | | 60.1 |
| Probiotic, 1 | 10 | 4.0 | | 61.6 | |
| Control, 2 | 7 | 9.9 | | | |
| Probiotic, 2 | 9 | 3.9 | 4.0 | 60.9 | |

*RPP is "relative percent protection" calculated 1 minus as the mean lice count divided by 5 the mean lice count on the reference control group × 100 (as percent).

The immersion in probiotic solution took place 12 days prior to challenge with copepodids of the genus *Lepeophtheirus salmonis* (30 copepodids/fish for 30 minutes with oxygenation). Two control groups, Ctrl-1 and Ctrl-2, unexposed to the probiotic composition,) were similarly set up and challenged with sea lice concurrently with the exposed fish.

Lice counting was carried out in all four groups at 28 days post challenge with sea lice. As can be seen in FIG. 1) the results show a significant reduction in attached lice and a lack of feeding in the attached lice in the two probiotic application groups (SB-1 and SB-2) compared to the two unexposed control groups (Ctrl-1 and Crl-2).

Example 2

Salmon (mean weight 150 g) were immersed for 35 min in a solution comprising a probiotic composition comprising *Aliivibrio* balderis and *Aliivibrio* njordis grown together ("Stembiont", $1.23 \times 10^{10}$ cfu/ml composition was used at a 1/20 dilution when bathing the fish) together with an anesthetic bath on Feb. 19, 2019, 159 days (5.5 months) before introduction of sea lice of the genus *Lepeophtheirus salmo-*

Table 2 shows Lice counts for treated and untreated groups (not cohabitant), and relative percent protection (RPP) 5.5 months after exposure to the probiotic composition.

TABLE 2

| Treatment | No. Fish | Tank | lice count on day 32 | Average count/Applic Group | RPP probiotic application |
|---|---|---|---|---|---|
| Probiotic comp. | 17 | 18 | 8.4 | 7.8 | 63.4 |
| Probiotic comp. | 23 | 13 | 7.4 | | |
| Control | 9 | 12 | 23.6 | 21.4 | |
| Control | 15 | 17 | 21.9 | | |
| Control | 10 | 11 | 18.6 | | |

The results demonstrate a marked effect from bathing the salmon in probiotic bacteria on the ability of the sea lice copepodids to attach to the skin of the salmon. The cohabitation of fish that were exposed to probiotic bacteria with fish that were not exposed leads to transfer of the protection from bathed fish to fish not exposed to the probiotc bacteria to a level close to or higher than 50% of the protection originally developed in the primarily exposed salmon after the primarily exposure to the probiotic bacteria. This transfer of protection occurs such a long time after exposure of the bathed fish to the probiotic bacteria so the transferred protection cannot be explained by leftover bacteria on the surface of the probiotic bathed fish. The protection of the cohabitant fish must come from probiotic bacteria or components of these probiotic bacteria secondarily excreted from the primarily exposed fish or from host factors excreted from the fish that were primarily exposed. The ectoparasite enhancement for protection in Example 2 was effective and confirmed the results in Example 1.

Example 3

Salmon 34 g were PIT tagged (see Example 2) and introduced to 180 L tanks 11.06.2019. A probiotic composition comprising *Aliivibrio* balderis and *Aliivibrio* njordis (Composition 1 in Table 3 below) or *Aliivibrio* balderis, *Aliivibrio* njordis, and *Aliivibrio* nannie (Composition 2 in Table 3 below) was used as preventive empowerment as below in Table 3 in individual 180 L tanks. The groups were used as part of a larger population (in the same manner as in examples 1 and 2).

For this example, *Aliivibrio* balderis and *Aliivibrio* njordis were co-cultured resulting in Composition 1 having about 30% A. balderis and about 70% A. njordis, while *Aliivibrio* nannie was cultured separately. To produce Composition 2, the A. nannie culture was added to Composition 1 resulting in a ratio of about 20% A. balderis and 47% A. njordis and about 33% A. nannie.

Composition 1 had a total bacterial count of about 7.2× $10^8$ CFU/ml, while the Composition 2 had a total bacterial count of about 8.8×$10^8$ CFU/ml. A 1/20 times dilution of Composition 1 and 2, respectively, was used for bathing the fish. The fish were bathed in the probiotic composition for 35 min.

To compare the effect of microbial enhancement to microbial depletion by use of an antimicrobial compound, Halamid (Chloramine T), fish in the microbial depletion group were given a Halamid treatment starting 17.06.2019 weekly for four weeks in freshwater. All groups were introduced to SW (salt water) 10.07.2019 and full SW 17.07.2019.

The Lice Challenge:

24.07.2019:15 Lice of the genus *Lepeophtheirus salmonis* was added per fish 15.08.2019: Lice attachment was checked and confirmed after 22 days 27.08.2019: Lice was counted 34 days after challenge The study included five different treatment groups in duplicate, i.e. a total of 10 tanks as seen in Table 3 below. For the lice treatment groups, 15 fish from each tank were moved to a separate holding tank and 15 lice per fish was added (number calculated by size).

TABLE 3

| | | Results per 27 Aug. 2019 | | |
|---|---|---|---|---|
| Tank | Treatment: | Lice number $1^{st}$ tank | Lice number $2^{nd}$ tank | Average |
| 1 and 6 | Control (untreated) | 1.60 | 2.80 | 2.20 |
| 2 and 7 | Composition 1 | 1.73 | 2.07 | 1.90 |
| 3 and 8 | Composition 2 | 1.93 | 1.67 | 1.80 |
| 4 and 9 | Untreated + Halamid weekly | 1.79 | 1.40 | 1.60 |

TABLE 3-continued

| | | Results per 27 Aug. 2019 | | |
|---|---|---|---|---|
| Tank | Treatment: | Lice number $1^{st}$ tank | Lice number $2^{nd}$ tank | Average |
| 5 and 10 | Composition 1 + Halamid weekly | 1.77 | 1.71 | 1.74 |

Conclusion.

In general, the total number of attached lice was very low.

There was a difference in the skin structure of fish treated with Composition 1 and 2 compared to the skin structure of untreated fish.

Lice normally bind from the dorsal fin and backwards, but in the probiotic enhanced groups they mostly attached to the head.

Some lice with lighter colors which appeared easier to remove were observed in the probiotic enhanced groups.

On 17.09.2019 fish were checked for lice egg strings.

When 52 of the total number of 150 fish were examined, only two lice were found, both in the Chalamus stage. This indicates that the lice have not evolved to the mature adult stage where egg strings evolve. Rather, the lice have detached when entering mobile adult stage (if they even reached adult stage).

Example 4

In this example the number of goblet cells in salmon with and without treatment with a probiotic composition was studied.

Atlantic salmon smolts were empowered with a probiotic bacterial composition comprising A. balderis and A. njordis in connection with the regular vaccination operation 8 weeks before the smolts were transferred to sea water (March 2018). The bacterial concentration in the composition was 1×10 $\log^7$ cfu/ml in the mixed probiotic culture before dilution and 1×10 $\log^6$ cfu/ml in the application water after dilution. The probiotic bacteria were grown together and the ratio between A. balderis and A. njordis in the resulting culture was about 70% and 30% respectively. The probiotic composition was added to the anaesthetic bath (30 mg Benzoak Vet. pr. liter) in a dilution of 1:20 and the presmolt stayed in the bath for 30 to 40 seconds before being automatically transferred to the vaccination robot.

The vaccinated presmolts were reared for 8 weeks before being transferred to sea water. The experienced personnel at the smolt plant commented that it had been many years since the smolts they reared had produced such a large layer of mucus when fish were handled. These observations encouraged further trials with sea lice prevention from probiotic empowerment.

A3 is a group of triploid fish treated with the probiotic composition and A2 is a group of diploid fish not treated by the probiotic composition. Both A3- and A2-groups are obtained from Ranfjord (Norway). B1-untreated and B1-treated are similar fish obtained from Grytågå (Norway). The number of goblet cells (mucus cells) was counted in skin samples from the head and body of seven fish from each batch. For each fish three polygonal areas between 0.2 mm$^2$ and 0.3 mm$^2$ of the epidermis (the outermost layer of the skin) were sampled, one from the head, two from different parts of the body. The specimens were coloured with Periodic Acid Shiff (PAS) for the goblet cells to be distinct in images. The digital images were analysed by a skilled investigator. All data passed the D'Agostino & Pearson normality test, Shapiro-Wilk normality test, Brown-Forsythe test and Bartlett's test. Tukey's multiple comparisons test showed significance (P<0.0008) between the A3- and the A2-group.

Figure 4:
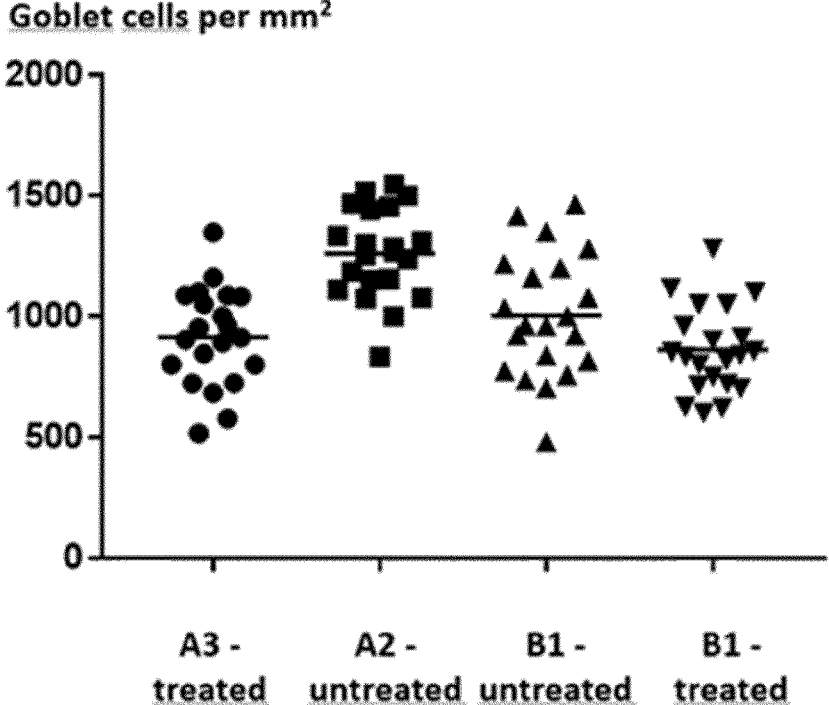
FIG. 4: Goblet cells in four experiments. The treated fish have fewer cells with more mucus.

FIG. 4 shows the number of goblet cells per square mm in salmon, analysed in GraphPad Prism v 7.03. The average number of goblet cells per $mm^2 \pm SD$ is: A3-treated: 914.7±203.7, A2-untreated: 1262±186.8, B1-untreated: 1004±257, B1-treated: 861.9±180.5.

The untreated fish have more, but smaller goblet cells. In the treated fish, there are fewer cells, but they are larger with more mucus. Without wishing to be bound by theory, the effect of this may be that the fish respond with an increased flow of mucus to an irritation from ectoparasites trying to attach to the skin or surface of the fish. Repeatedly it is observed that when fish, including different species as Atlantic salmon and lump fish, are being exposed to probiotic bath are markedly much more calm/less anxious than the fish in parallel unexposed fish tanks. This effect seems to be continuing for a long time after probiotic enhancement and may explain that the fish are not discharging their goblet cells for mucus content as they do when they are stressed or panicking. As an interesting parallell it is regularliy observed that when Atlantic salmon populations are artificially challenged with pathogenic bacteria as *Moritella viscosa* they are panicking trying to escape the added bacterial culture within seconds after the water has been loaded with the bacterial culture. This observation is then monid Anemia Virus (ISAv) and Infectious Pancreatic Necrosis virus (IPNv) at Cargill Innovation Center (CIC) laboratory, Colaco, Chile before entering the study.

None of the fish in the study had been treated with antibiotics and were deemed clinically healthy, meaning they had no condition causing an impediment to mobility or feeding, i.e., fish had good quality fins and good body condition. Any sexually matured, injured or deformed fish and fish that did not appear to be fully smoltified were excluded from the study upon arrival or during distribution in study tanks.

Fish were transported from the Cargill Innovation Center (CIC) hatchery into VESO Chile's Challenge Room and was acclimated for at least 5 days in seawater according to C-2023. Fish and tanks were tended to and monitored on a daily basis according to C-2002 and C-2004. Fish were fed via automatic feeders (1-2% of the biomass each day) using feed provided by CIC. Salinity was 29-35%. (sea water). Fish enrolled in the trial were assessed for gill Na+/K+ ATPase values at an external laboratory to confirm smolt status. Fish were deemed smoltified according to ATPase values recorded in fish batch ST1903. Environmental parameters such as temperature and oxygen saturation inside each tank, salinity and pH in header tank were recorded automatically. Any abnormal or unexpected behaviour, loss of appetite or any unexpected increase in mortality was immediately attended to.

240 fish with a weight of 112.1±10.1 g were divided into three tanks with 80 fish per tank. The fish were bred and treated under conditions as shown in Table 4.

TABLE 4

| | | Allocation of fish during acclimation and seeding/ immunization period and environmental parameters | | | | | |
|---|---|---|---|---|---|---|---|
| Tank ID | Group | Test/control substance(s) | Tank volume (L) | Fish (N)* | Density $(kg/m^3)$ | Temperature (° C.) | Salinity (‰) |
| B1 | Group 1 | Stembiont 1 | 500 | 80 | 17.9 | 11.9 ± 0.3 | 32 |
| B2 | Group 2 | Stembiont 2 | 500 | 80 | 17.9 | 11.9 ± 0.3 | 32 |
| B3 | Group 3 | Control (seawater) | 500 | 80 | 17.9 | 11.9 ± 0.3 | 32 | diametrically opposite to the behaviour of the fish when they are exposed to these probiotic bacteria.

These observations may indicate and support the theory that reduced stress levels are primarily an important reason for a larger reserve of mucus to react locally on the skin against attacking sea lice resulting in reduced sea lice levels in fish exposed to these probiotic bacteria.

Example 5

A study was designed to assess in vivo efficacy of microbial test substances against sea lice (*Caligus rogercresseyi*) at chalimus and adult/motile stages on Atlantic salmon post-smolts in Pacific sea water. Efficacy was estimated against a mock handled control group (negative control group). The study was comprised of two treatment groups and one control group.

Atlantic salmon (*Salmo salar*), post-smolts of the strain "Stofnfiskur" originating from Iceland were used in the study. All fish participating in the study were unvaccinated and the infectious status of the fish and/or egg origin was documented to be negative for the following pathogens: *P. salmonis, Renibacterium salmoninarum, Flavobacterium psychrophilum*, Piscine orthoreovirus (PRV), Infectious Sal- The tanks had a dissolved oxygen saturation of >84% inside the tanks with a 1.0-1.2 tank water turnover/h during acclimation and sea lice challenge. Tanks were cleaned once a day and were flushed only if required. The photoperiod was 24 h Daylight and 0 h dark.

Treatment Bath

The test and control substances (Stembiont 1, Stembiont 2) were delivered on a ready-to-use form. Storage and transport in refrigerated conditions up to 4 weeks is allowed for the commercial use of Stembiont, and the following batches were used within that time limit. The Stembiont 1 bacterial composition comprised a mixed culture of *Aliivibrio* balderis and *Aliivibrio* njordis grown together in LB with 2,5% salt (total concentration about $4 \times 10^9$ cfu per ml of which about 60% was A. njordis and about 40% was A. balderis). Stembiont 2 was a bacterial composition comprising a mixed culture of *Aliivibrio* balderis and *Aliivibrio* njordis grown together as for Stembiont 1 above, but mixed with *Aliivibrio* nannie which was cultured separately under same conditions as A. njordis and A. balderis. The final Stembiont 2 composition had a final concentration about $5.2 \times 10^9$ cfu per ml of which about 40% was A. njordis, about 27% was A. balderis and about 33% was A. nannie. Test substances were kept refrigerated before use and taken out of refrigeration and acclimated to the rearing water temperature (12° C.) before use.

Prior to bath empowerment fish were starved for 24 hours and netted and transferred to the treatment bath with a low dose of the anesthetic benzocaine according to C-1012. During treatment, fish were submerged in a bucket containing clean seawater and the added test compounds (Group1: Stembiont 1, Group 2: Stembiont 2) in batches of fish per net. The ratio of test product in the bucket was 1 part of Stembiont to 19 parts seawater in the rearing seawater. The bath lasted for 90 seconds after which fish were distributed into their corresponding study tanks. Control/mock group were handled similarly with clean sea water. The day of Stembiont baths is defined as study Day 0.

Lice Challenge

Study fish were challenged once with sea lice copepodites 35 days after the Stembiont bath and mock bath treatments.

Fish were starved for 24 hours before challenge. Fish were challenged according to VESO standard procedure (C-1056) in the challenge tank(s) at controlled temperature (11.7° C.) in sea water (32% %) with *C. rogercresseyi* copepodids delivered by Sea Lice Lab at Cargill Innovation Center (CIC). On challenge day, the water flow was stopped, and water level was lowered to reach a fish density between 60-80 kg/m³; tank lights were turned-off and tank window covered. The fish were challenged by adding on the surface *C. rogercresseyi* copepodids to the tank at a ratio of 35 copepodids per fish. For the sea lice challenge, sea lice load was recorded at 13 days post infection (dpi) and 27 dpi aiming chalimus and adult/motile stages, respectively. The sea lice challenge was successful since average lice per fish, considering all study fish at 13 dpi, was 23.1±6.7 lice/fish and infestation success was 66%.

Fish density/water level was maintained according to C-1056. During this period the lights in tanks were kept off and oxygenation system maintaining levels aimed to at least 70% saturation during the whole challenge. After 2 hours, the water level was raised to approx. 0.3 m³ and then to 0.5 m³. After 5 hours, the water turnover was re-established and maintained at 0.8 tank/h for 18 h.

Chalimus and Adult/Motile Lice Counting

Fish were anaesthetized with Isoeugenol 50% for lice counting according to C-1012; at samplings fish were euthanized with benzocaine according to C-1059. Loose lice recorded in the sampling bucket were counted and allocated/distributed to sampled fish and fish group. For sessile stage counting, i.e. chalimus stages, 20 fish were sampled, lice recorded and eliminated; thus, 60 fish remained for final counting at adult stage in each study tank. The number of chalimus and adult/motile lice was counted on 13 and 27 days respectively after challenge. No fish during acclimation, seeding and challenge period suffered severe damage resulting from handling or lice challenge. No fish died or suffered from severe wounds, eye and/or skin damage resulting from lie infestation during challenge.

Results

Figure 5:
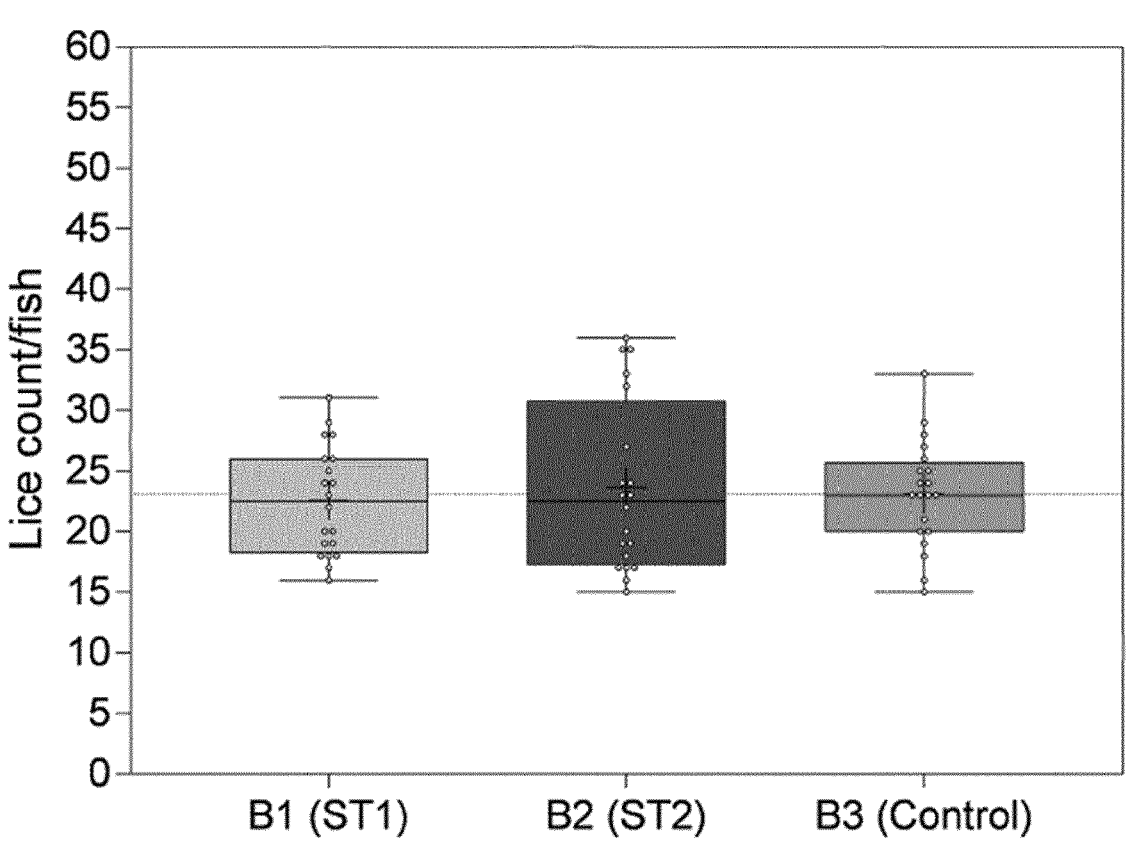
FIG. 5: Lice counting at chalimus stage performed on 13 dpi (S1).
Figure 6:
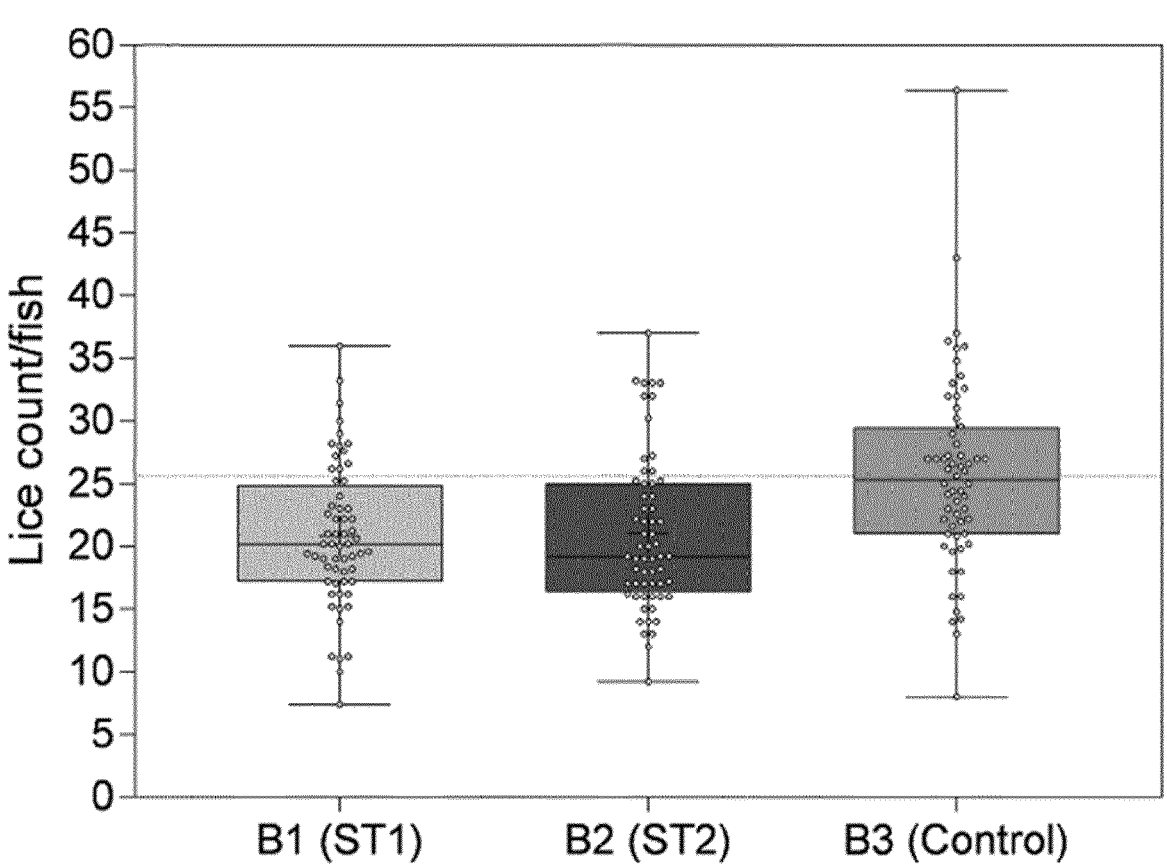
FIG. 6: Lice counting at adult/motile lice performed on 27 dpi (S2).

Lice counting at chalimus stage was performed on 13 dpi (S1) and at adult/motile lice was performed on 27 dpi (S2). Results are shown in FIGS. 5 and 6, Tables 5 and 6.

TABLE 5

Lice records 13 dpi (S1)

| Treatment | Tank | No of fish | Aver. | SD | Median | min | max |
|---|---|---|---|---|---|---|---|
| Control | B3 | 20 | 23.1 | 4.4 | 23.0 | 15 | 33 |
| Stembiont 1 (ST1) | B1 | 20 | 22.6 | 4.5 | 22.5 | 16 | 31 |
| Stembiont 2 (ST2) | B2 | 20 | 23.6 | 7.0 | 22.5 | 15 | 36 |

TABLE 6

Lice records at 27 dpi (S2)*

| Treatment | Tank | No of fish | Aver. | SD | Median | min | max |
|---|---|---|---|---|---|---|---|
| Control | B3 | 60 | 25.7 | 7.8 | 25.3 | 8.0 | 56.4 |
| Stembiont 1 (ST1) | B1 | 60 | 20.8 | 5.7 | 20.2 | 7.4 | 36.0 |
| Stembiont 2 (ST2) | B2 | 60 | 20.9 | 6.2 | 19.2 | 9.2 | 37.0 |

*loose lice in anaesthetic bucket were allocated to sampled fish (e.g. to 5 fish)

Relative and absolute efficacy of Stembiont bath treatments at Chalimus stages (S1, 13 dpi) and adult stages (S2, 27 dpi) are shown in Table 7.

TABLE 7

Relative and absolute efficacy of Stembiont treatment at 13 dpi (S1) and 27 dpi (S2).

| | Average louse | | Relative efficacy[3] (%) | | Absolute efficacy[4] (%) | |
|---|---|---|---|---|---|---|
| Treatment | S1 13 dpi | S2 27 dpi | S1 13 dpi | S2 27 dpi | S1 13 dpi | S2 27 dpi |
| Stembiont 1 (ST1) | 22.6 | 20.8 | 2.2% | 19.1% | — | 8.0% |
| Stembiont 2 (ST2) | 23.6 | 20.9 | −2.2% | 18.7% | — | 11.4% |

[3]Relative efficacy was estimated as (1-(average No. of lice in treated group at each sampling point/average No. of lice in control group at each sampling point)) × 100
[4]Absolute efficacy was estimated as (1-(average No. of lice in treated group at S2/average No. of lice in treated group at S1)) × 100

Example 5 demonstrates that the probiotic treatment is effective for another ectoparasite, in different sea water than the challenge and environment in the other four examples.

Example 6

A study to monitor the effect of the probiotic bacteria directly on lice was performed by exposure of sea lice copepodids (Lepeophteirus *salmonis*) and monitoring the behavior and mortality of the sea lice.

The three probiotic bacteria A. njordis, A. balderis and A. nannie were added to glass containers with 10 copepodids at a temperature of 12° C. The copepodids were exposed to the bacteria for 24 hours before reading of the results. The experiments were set up with three glass containers without extra air supply to the water and with air supply to the water. No lice died after exposure to the probiotic bacteria.

As controls to the experiment sea lice copepodids were exposed to known fish pathogenic bacteria in the same way. The bacteria used were *Aliivibrio salmonicida, Aliivibrio wodanis, Moritella viscosa, Aliivibrio* friggiae and *Aliivibrio heliae*. A. friggiae and *A. heliae* killed all the copepodids while *A. salmonicida* and *M. viscosa* killed 50% of the copepodids. *A. wodanis* did not kill any of the copepodids.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Unless expressly described to the contrary, each of the preferred features described herein can be used in combination with any and all of the other herein described preferred features.

REFERENCES

WO 2019/135009.

ITEMS

1. A probiotic composition comprising probiotic bacteria of the species *Aliivibrio* njordis and/or *Aliivibrio* balderis for use in the treatment and/or prevention of an ectoparasitic infestation and/or gill parasite infection in a teleost.
2. The probiotic composition for use according to item 1, wherein said probiotic composition comprises probiotic bacteria of both *Aliivibrio* njordis and *Aliivibrio* balderis.
3. The probiotic composition for use according to item 1 or 2, wherein said Allivibrio njordis is *Aliivibrio* njordis strain B1-25, 18-1/2013 mandib V11, which has been deposited at National Collection of Industrial and Marine Bacteria and has been assigned accession number NCIMB 42593.
4. The probiotic composition for use of any one of the preceding items, wherein said *Aliivibrio* balderis is *Aliivibrio* balderis B1-24, 18-1/2013 kidn V12, which has been deposited at National Collection of Industrial and Marine Bacteria and has been assigned accession number NCIMB 42592.
5. The probiotic composition for use according to any one of the preceding items, wherein said probiotic composition further comprises probiotic bacteria of the species *Aliivibrio* nannie, such as *Aliivibrio* nannie B8-24, 313/2013 kidn V13, which has been deposited at National Collection of Industrial and Marine Bacteria and has been assigned accession number NCIMB 42594.
6. The probiotic composition for use according to any one of the preceding items, wherein said probiotic composition further comprises probiotic bacteria of the species *Psychrobacter* piscimesodermis, *Psychrobacter* piscimesenchymalis, *Psychrobacter* piscisubcutanea, *Pseudomonas* salmosubcutaneae, *Pseudomonas* salmosubpectoralis and/or *Pseudomonas* salmointermuscularis.
7. The probiotic composition for use according to item 6, wherein said *Psychrobacter* piscimesodermis is *Psychrobacter* piscimesodermis Fisk 1, 41, 6/3-2014 Atl. Salm, which has been deposited at National Collection of Industrial and Marine Bacteria and has been assigned accession number NCIMB 42947.
8. The probiotic composition for use according to item 6 or 7, wherein said *Psychrobacter* piscimesenchymalis is *Psychrobacter* piscimesenchymalis Fisk 2, 42, 6/3-2014 Atl. salm, which has been deposited at National Collection of Industrial and Marine Bacteria and has been assigned accession number NCIMB 42948.
9. The probiotic composition for use according to any one of items 6-8, wherein said *Psychrobacter* piscisubcutanea is *Psychrobacter* piscisubcutanea Fisk 3, 43, 6/3-2014 Atl. Salm, which has been deposited at National Collection of Industrial and Marine Bacteria and has been assigned accession number NCIMB 42949.

10. The probiotic composition for use according to any one of items 6-9, wherein said *Pseudomonas* salmosubcutaneae is *Pseudomonas* salmosubcutaneae Fisk 3, 13/5-2014, hb, Atl. Salm, which has been deposited at National Collection of Industrial and Marine Bacteria and has been assigned accession number NCIMB 43330.
11. The probiotic composition for use according to any one of items 6-10, wherein said *Pseudomonas* salmosubpectoralis is *Pseudomonas* salmosubpectoralis Fisk 3, 13/5-2014, ba, Atl. salm., which has been deposited at National Collection of Industrial and Marine Bacteria and has been assigned accession number NCIMB 43331.
12. The probiotic composition for use according to any one of items 6-11, wherein said *Pseudomonas* salmointermuscularis is *Pseudomonas* salmointermuscularis Fisk 4, 13/5-2014, ha, Atl. salm., which has been deposited at National Collection of Industrial and Marine Bacteria and has been assigned accession number NCIMB 43332.
13. The probiotic composition for use according to item 1 or 2, wherein said probiotic composition is administered to said teleost before, during or after administration of one or more further probiotic composition(s) comprising one or more of a probiotic bacterium as defined in any one of items 3-12.
14. The probiotic composition for use according to any one of the preceding items, wherein said probiotic composition comprises probiotic bacteria of two or more different strains of the same bacterial species.
15. The probiotic composition for use according to any one of the preceding items, wherein said teleost is a marine teleost.
16. The probiotic composition for use according to any one of items 1-14, wherein said teleost is a fresh water teleost.
17. The probiotic composition for use according to any one of the preceding items, wherein said teleost is of the family Salmonidae, such as salmon, trout, and chars.
18. The probiotic composition for use according to item 16, wherein said teleost of the family Salmonidae is Atlantic salmon (*Salmo salar*), brown trout (sea trout: *Salmo trutta*), Arctic char (*Salvelinus alpinus*), and/or any species of Pacific salmon, such as (Coho (Silver) salmon (*Oncorhynchus kisutch*), Chinook (King) (*Oncorhynchus tshawytscha*), pink (Humpy) salmon (*Oncorhynchus gorbuscha*), chum (Dog) salmon (*Oncorhynchus keta*), sockeye (*Oncorhynchus nerka*), cutthroat (*Oncorhynchus clarki clarki*) and steelhead (rainbow trout) (*Oncorhynchus mykiss*).
19. The probiotic composition for use according to any one of items 1-16, wherein said teleost is Atlantic cod, cleaner fish like lump fish and wrasses and freshwater fish as carps and perch.
20. The probiotic composition for use according to any one of the preceding items, wherein the ectoparasitic infestation is caused by sea lice.
21. The probiotic composition for use according to item 20, wherein the sea lice is of the genera *Lepeophtheirus*, such as *L. salmonis*, and/or *Caligus*, such as *C. rogercresseyi* and/or *C. elongatus*.

22. The probiotic composition for use according to any one of items 1-19, wherein said gill parasite infection is caused by an amoeba, such as an amoeba of the genus Neoparamoeba, such as Neoparamoeba perurans, an ectoparasite of the genus *Gyrodactylus*, such as *Gyro-dactylus salaris*, an ectoparasite of the genus Crypto-caryon, such as Cryptocaryon *irritans*, an ectoparasite of the genus *Lernaeocera*, such as *Lernaeocera bran-chialis*, an ectoparasite of the genus *Pseudorhabdo-synochus*, and/or an ectoparasite of the genus Amy-loodinium.

23. The probiotic composition for use according to any one of the preceding items, wherein said probiotic composition further comprises a pharmaceutically acceptable excipient and/or adjuvant.

24. The probiotic composition for use according to any one of the preceding items, wherein said probiotic composition is administered in combination with a chemical parasitic infection treatment agent, such as an organophosphate, a carbamate, a pyrethroid, a payre-thrin, a synergist, an insect growth regulating chemical and/or an avermectin.

25. The probiotic composition for use according to any one of the preceding items, wherein said probiotic composition is administered via bath or dip adminis-tration in salt, fresh or brackish water, by oral admin-istration, by oral administration or by injection, such as by intraperitoneal administration, intramuscular admin-istration, or subcutaneous administration.

26. The probiotic composition for use according to item 25, wherein said bath administration takes place for a time period of from 1 second to 5 hours, such as from 1 second to 2 hours, such as from 1 second to 1 hour, such as from 30 seconds to 1 hour or from 1 minute to 30 minutes.

27. The probiotic composition for use according to any one of the preceding items, wherein the total concen-tration of bacteria in the probiotic composition is from $10^2$ to $10^{14}$, such as from $10^8$ to $10^{13}$, from $10^9$ to $10^{13}$, from $10^{10}$ to $10^{12}$, from $10^2$ to $10^7$, or from $10^5$ to $10^7$.

28. The probiotic composition for use according to any one of the preceding items, wherein said probiotic composition is administered at least 10 days, such as at least 15 days, 20 days, 25 days, 30 days, or 40 days, before exposure of the teleost to the ectoparasite and/or gill parasite.

29. Use of probiotic bacteria of one or both of the species *Aliivibrio* njordis and *Aliivibrio* balderis for the prepa-ration of a medicament in the form of a probiotic composition for the treatment and/or prevention of an ectoparasitic infestation and/or and gill parasite infec-tion in a teleost.

30. The use according to item 29, wherein said probiotic composition comprises probiotic bacteria of both *Aliivibrio* njordis and Allivibrio balderis.

31. The use according to item 29 or 30, wherein said *Aliivibrio* njordis is *Aliivibrio* njordis strain B1-25, 18-1/2013 mandib V11, which has been deposited at National Collection of Industrial and Marine Bacteria and has been assigned accession number NCIMB 42593

32. The use according to any one items 29-31, wherein said *Aliivibrio* balderis is *Aliivibrio* balderis B1-24, 18-1/2013 kidn V12, which has been deposited at National Collection of Industrial and Marine Bacteria and has been assigned accession number NCIMB 42592.

33. The use according to any one of items 29-32, wherein said probiotic composition further comprises probiotic bacteria of the species *Aliivibrio* nannie, such as *Aliivi-brio* nannie B8-24, 313/2013 kidn V13, which has been deposited at National Collection of Industrial and Marine Bacteria and has been assigned accession num-ber NCIMB 42594.

34. The use according to any one of items 29-33, wherein said medicament further comprises probiotic bacteria of the species *Psychrobacter* piscimesodermis, *Psy-chrobacter* piscimesenchymalis, *Psychrobacter* pisci-subcutanea, *Pseudomonas* salmosubcutaneae, *Pseudomonas* salmosubpectoralis and/or *Pseudomonas* salmointermuscularis.

35. The use according to item 34, wherein said *Psychro-bacter* piscimesodermis is *Psychrobacter* piscimeso-dermis Fisk 1, 41, 6/3-2014 Atl. Salm, which has been deposited at National Collection of Industrial and Marine Bacteria and has been assigned accession num-ber NCIMB 42947.

36. The use according to item 34 or 35, wherein said *Psychrobacter* piscimesenchymalis is *Psychrobacter* piscimesenchymalis Fisk 2, 42, 6/3-2014 Atl. salm, which has been deposited at National Collection of Industrial and Marine Bacteria and has been assigned accession number NCIMB 42948.

37. The use according to any one of items 34-36, wherein said *Psychrobacter* piscisubcutanea is *Psychrobacter* piscisubcutanea Fisk 3, 43, 6/3-2014 Atl. Salm, which has been deposited at National Collection of Industrial and Marine Bacteria and has been assigned accession number NCIMB 42949.

38. The use according to any one of items 34-37, wherein said *Pseudomonas* salmosubcutaneae is *Pseudomonas* salmosubcutaneae Fisk 3, 13/5-2014, hb, Atl. Salm, which has been deposited at National Collection of Industrial and Marine Bacteria and has been assigned accession number NCIMB 43330.

39. The use according to any one of items 34-38, wherein said *Pseudomonas* salmosubpectoralis is *Pseudomonas* salmosubpectoralis Fisk 3, 13/5-2014, ba, Atl. salm., which has been deposited at National Collection of Industrial and Marine Bacteria and has been assigned accession number NCIMB 43331.

40. The use according to any one of items 34-39, wherein said *Pseudomonas* salmointermuscularis is *Pseudomo-nas* salmointermuscularis Fisk 4, 13/5-2014, ha, Atl. salm., which has been deposited at National Collection of Industrial and Marine Bacteria and has been assigned accession number NCIMB 43332.

41. Use of a a probiotic composition as defined in item 1 or 2 and a probiotic composition comprising one or more of a probiotic bacterium as defined in any one of items 3-12 for the preparation of a medicament in the form of a probiotic composition for the treatment and/or prevention of an ectoparasitic infestation or gill parasite infection in a teleost, wherein said probiotic composition as defined in item 1 or 2 is administered to said teleost before, during or after administration of one or more further probiotic composition(s) comprising a probiotic bacterium as defined in any one of items 3-12.

42. The use according to any one of items 29-41, wherein said probiotic composition comprises probiotic bacteria of two or more different strains of the same bacterial species.

43. The use according to any one of items 29-42, wherein said teleost is a marine teleost.

44. The use according to any one of items 29-42, wherein said teleost is a fresh water teleost.

45. The use according to any one of items 29-44, wherein said teleost is of the family Salmonidae, such as salmon, trout, and chars.

46. The use according to item 45, wherein said teleost of the family Salmonidae is Atlantic salmon (*Salmo salar*), brown trout (sea trout: *Salmo trutta*), Arctic char (*Salvelinus alpinus*), and/or any species of Pacific salmon, such as (Coho (Silver) salmon (*Oncorhynchus kisutch*), Chinook (King) (*Oncorhynchus tshawytscha*), pink (Humpy) salmon (*Oncorhynchus gorbuscha*), chum (Dog) salmon (*Oncorhynchus keta*), sockeye (*Oncorhynchus nerka*), cutthroat (*Oncorhynchus clarki clarki*) and steelhead (rainbow trout) (*Oncorhynchus mykiss*).

47. The use according to any one of items 29-44, wherein said teleost is Atlantic cod, cleaner fish such as lump fish and wrasses and freshwater fish as carps and perch.

48. The use according to any one of items 29-47, wherein the ectoparasitic infection is caused by a sea lice.

49. The use according to item 48, wherein the sea lice is of the genera *Lepeophtheirus*, such as *L. salmonis*, and/or *Caligus*, such as *C. rogercresseyi* and/or *C. elongatus*.

50. The use according to any one of items 29-47, wherein said gill parasite infection is caused by an amoeba, such as an amoeba of the genus Neoparamoeba, such as Neoparamoeba perurans, an ectoparasite of the genus *Gyrodactylus*, such as *Gyrodactylus salaris*, an ectoparasite of the genus Cryptocaryon, such as Cryptocaryon *irritans*, an ectoparasite of the genus *Lernaeocera*, such as *Lernaeocera branchialis*, an ectoparasite of the genus *Pseudorhabdosynochus*, and/or an ectoparasite of the genus Amyloodinium.

51. The use according to any one of items 29-50, wherein said probiotic composition further comprises a pharmaceutically acceptable excipient and/or adjuvant.

52. The use according to any one of items 29-51, wherein said probiotic composition is administered in combination with a chemical parasitic infection treatment agent, such as an organophosphate, a carbamate, a pyrethroid, a pyrethrin, a synergist, an insect growth regulating chemical and/or an avermectin.

53. The use according to any one of items 29-52, wherein said probiotic composition is administered via bath or dip administration in salt, fresh or brackish water, by oral administration, by oral administration or by injection, such as by intraperitoneal administration, intramuscular administration, or subcutaneous administration.

54. The use according to item 53, wherein said bath administration takes place for a time period of from 1 second to 5 hours, such as from 1 second to 2 hours, such as from 1 second to 1 hour, such as from 30 seconds to 1 hour or from 1 minute to 30 minutes.

55. The use according to any one of items 29-54, wherein the total concentration of bacteria in the probiotic composition is from $10^2$ to $10^{14}$, such as from $10^8$ to $10^{13}$ from $10^9$ to $10^{13}$, from $10^{10}$ to $10^{12}$, from $10^2$ to $10^7$, or from $10^5$ to $10^7$.

56. The use according to any one of items 29-55, wherein said probiotic composition is administered at least 10 days, such as at least 15 days, 20 days, 25 days, 30 days, or 40 days, before exposure of the teleost to the ectoparasite and/or gill parasite.

57. A method for treating and/or preventing an ectoparasitic infestation and/or gill parasite infection in a teleost, said method comprising administering a therapeutically effective amount of a probiotic composition comprising probiotic bacteria of one or both of the species *Aliivibrio* njordis and *Aliivibrio* balderis to a teleost in need thereof.

58. The method according to item 57, wherein said probiotic composition comprises probiotic bacteria of both *Aliivibrio* njordis and *Aliivibrio* balderis.

59. The method according to item 57 or 58, wherein said *Aliivibrio* njordis is *Aliivibrio* njordis strain B1-25, 18-1/2013 mandib V11, which has been deposited at National Collection of Industrial and Marine Bacteria and has been assigned accession number NCIMB 42593.

60. The method according to any one items 57-59, wherein said *Aliivibrio* balderis is *Aliivibrio* balderis B1-24, 18-1/2013 kidn V12, which has been deposited at National Collection of Industrial and Marine Bacteria and has been assigned accession number NCIMB 42592.

61. The method according to any one items 57-60, wherein said probiotic composition further comprises probiotic bacteria of the species *Aliivibrio* nannie, such as *Aliivibrio* nannie B8-24, 313/2013 kidn V13, which has been deposited at National Collection of Industrial and Marine Bacteria and has been assigned accession number NCIMB 42594.

62. The method according to any one items 57-61, wherein said probiotic composition further comprises probiotic bacteria of the species *Psychrobacter* piscimesodermis, *Psychrobacter* piscimesenchymalis, *Psychrobacter* piscisubcutanea, *Pseudomonas* salmosubcutaneae, *Pseudomonas* salmosubpectoralis and/or *Pseudomonas* salmointermuscularis.

63. The method according to item 62, wherein said *Psychrobacter* piscimesodermis is *Psychrobacter* piscimesodermis Fisk 1, 41, 6/3-2014 Atl. Salm, which has been deposited at National Collection of Industrial and Marine Bacteria and has been assigned accession number NCIMB 42947.

64. The method according to item 62 or 63, wherein said *Psychrobacter* piscimesenchymalis is *Psychrobacter* piscimesenchymalis Fisk 2, 42, 6/3-2014 Atl. salm, which has been deposited at National Collection of Industrial and Marine Bacteria and has been assigned accession number NCIMB 42948.

65. The method according to any one of items 63-64, wherein said *Psychrobacter* piscisubcutanea is *Psychrobacter* piscisubcutanea Fisk 3, 43, 6/3-2014 Atl. Salm, which has been deposited at National Collection of Industrial and Marine Bacteria and has been assigned accession number NCIMB 42949.

66. The method according to any one of items 62-65, wherein said *Pseudomonas* salmosubcutaneae is *Pseudomonas* salmosubcutaneae Fisk 3, 13/5-2014, hb, Atl. Salm, which has been deposited at National Collection of Industrial and Marine Bacteria and has been assigned accession number NCIMB 43330.

67. The method according to any one items 62-66, wherein said *Pseudomonas* salmosubpectoralis is *Pseudomonas* salmosubpectoralis Fisk 3, 13/5-2014, ba, Atl. salm., which has been deposited at National Collection of Industrial and Marine Bacteria and has been assigned accession number NCIMB 43331.

68. The method according to any one of items 62-67, wherein said *Pseudomonas* salmointermuscularis is *Pseudomonas* salmointermuscularis Fisk 4, 13/5-2014, ha, Atl. salm., which has been deposited at National Collection of Industrial and Marine Bacteria and has been assigned accession number NCIMB 43332.

69. The method according to any one of items 57-68, said method comprising administering a probiotic composition as defined in item 1 or 2 to said teleost before, during or after administration of one or more further probiotic composition(s) comprising one or more of a probiotic bacterium as defined in any one of items 3-12.

70. The method according to any one items 57-69, wherein said probiotic composition comprises probiotic bacteria of two or more different strains of the same bacterial species.

71. The method according to any one items 57-70, wherein said teleost is a marine teleost.

72. The method according to any one items 57-70, wherein said teleost is a fresh water teleost.

73. The method according to any one items 57-72, wherein said teleost is of the family Salmonidae, such as salmon, trout, and chars.

74. The method according to item 73, wherein said teleost of the family Salmonidae is Atlantic salmon (*Salmo salar*), brown trout (sea trout: *Salmo trutta*), Arctic char (*Salvelinus alpinus*), and/or any species of Pacific salmon, such as (Coho (Silver) salmon (*Oncorhynchus kisutch*), Chinook (King) (*Oncorhynchus tshawytscha*), pink (Humpy) salmon (*Oncorhynchus gorbuscha*), chum (Dog) salmon (*Oncorhynchus keta*), sockeye (*Oncorhynchus nerka*), cutthroat (*Oncorhynchus clarki clarki*) and steelhead (rainbow trout) (*Oncorhynchus mykiss*).

75. The method according to any one items 57-72, wherein said teleost is Atlantic cod, cleaner fish like lump fish and wrasses and freshwater fish as carps and perch.

76. The method according to any one items 57-75, wherein the ectoparasitic infection is caused by a sea lice.

77. The method according to item 76, wherein the sea lice is of the genera *Lepeophtheirus*, such as *L. salmonis*, and/or *Caligus*, such as *C. rogercresseyi* and/or *C. elongatus*.

78. The method according to any one items 57-77, wherein said gill parasite infection is caused by an amoeba, such as an amoeba of the genus Neoparamoeba, such as Neoparamoeba perurans, an ectoparasite of the genus *Gyrodactylus*, such as *Gyrodactylus salaris*, an ectoparasite of the genus Cryptocaryon, such as Cryptocaryon *irritans*, an ectoparasite of the genus *Lernaeocera*, such as *Lernaeocera branchialis*, an ectoparasite of the genus *Pseudorhabdosynochus*, and/or an ectoparasite of the genus Amyloodinium.

79. The method according to any one items 57-78, wherein said probiotic composition further comprises a pharmaceutically acceptable excipient and/or adjuvant.

80. The method according to any one items 57-79, wherein said probiotic composition is administered in combination with a chemical parasitic infection treatment agent, such as an organophosphate, a carbamate, a pyrethroid, a payrethrin, a synergist, an insect growth regulating chemical and/or an avermectin.

81. The method according to any one items 57-80, wherein said probiotic composition is administered via bath or dip administration in salt, fresh or brackish water, by oral administration, by oral administration or by injection, such as by intraperitoneal administration, intramuscular administration, or subcutaneous administration.

82. The method according to item 81, wherein said bath administration takes place for a time period of from 1 second to 5 hours, such as from 1 second to 2 hours, such as from 1 second to 1 hour, such as from 30 seconds to 1 hour or from 1 minute to 30 minutes.

83. The method according to any one of items 57-82, wherein the total concentration of bacteria in the probiotic composition is from $10^2$ to $10^{14}$, such as from $10^8$ to $10^{13}$, from $10^9$ to $10^{13}$, from $10^{10}$ to $10^{12}$, from $10^2$ to $10^7$, or from $10^5$ to $10^7$.

84. The method according to any one of items 57-83, wherein said probiotic composition is administered at least 10 days, such as at least 15 days, 20 days, 25 days, 30 days, or 40 days, before exposure of the teleost to the ectoparasite and/or gill parasite.

The invention claimed is:

1. A method for treating and/or preventing an ectoparasitic infestation and/or gill parasite infection in a teleost, said method comprising administering a therapeutically effective amount of a probiotic composition comprising probiotic bacteria of the species *Aliivibrio* njordis and/or *Aliivibrio* balderis, and optionally *Aliivibrio* nannie, to a teleost in need thereof;

wherein said probiotic composition further comprises probiotic bacteria of the species *Psychrobacter* piscimesodermis, *Psychrobacter* piscimesenchymalis, *Psychrobacter* piscisubcutanea, *Pseudomonas* salmosubcutaneae, *Pseudomonas* salmosubpectoralis and/or *Pseudomonas* salmointermuscularis; or wherein said probiotic composition is administered to said teleost before, during or after administration of one or more further probiotic composition(s) comprising one or more of a probiotic bacterium of the species *Psychrobacter* piscimesodermis, *Psychrobacter* piscimesenchymalis, *Psychrobacter* piscisubcutanea, *Pseudomonas* salmosubcutaneae, *Pseudomonas* salmosubpectoralis and/or *Pseudomonas* salmointermuscularis.

2. The method according to claim 1, wherein said teleost is a marine teleost.

3. The method according to claim 1, wherein said teleost is a fresh water teleost.

4. The method according to claim 1, wherein said teleost is of the family Salmonidae.

5. The method according to claim 4, wherein said teleost of the family Salmonidae is Atlantic salmon (*Salmo salar*), brown trout (sea trout: *Salmo trutta*), Arctic char (*Salvelinus alpinus*), and/or any species of Pacific salmon.

6. The method according to claim 5, wherein said teleost is Coho (Silver) salmon (*Oncorhynchus kisutch*), Chinook (King) (*Oncorhynchus tshawytscha*), pink (Humpy) salmon (*Oncorhynchus gorbuscha*), chum (Dog) salmon (*Oncorhynchus keta*), sockeye (*Oncorhynchus nerka*), cutthroat (*Oncorhynchus clarki clarki*) or steelhead (rainbow trout) (*Oncorhynchus mykiss*).

7. The method according to claim 4, wherein the teleost of the family Salmonidae is salmon, trout or chars.

8. The method according to claim 1, wherein said teleost is Atlantic cod, cleaner fish or freshwater fish.

9. The method according to claim 8, wherein the cleaner fish is lump fish or wrasse, and/or wherein the freshwater fish is carps or perch.

10. The method according to claim 1, wherein the ectoparasitic infestation is caused by a sea louse.

11. The method according to claim 10, wherein said sea louse is of the genera *Lepeophtheirus*, or is *Lepeophtheirus salmonis*; and/or wherein said sea louse is of the genera *Caligus*, or is *Caligus rogercresseyi* and/or *Caligus elongatus*.

12. The method according to claim 1, wherein said ectoparasitic infestation is caused by an amoeba an ectoparasite of the genus *Gyrodactylus*, an ectoparasite of the genus Cryptocaryon, an ectoparasite of the genus *Lernaeocera*, an ectoparasite of the genus *Pseudorhabdosynochus*, and/or an ectoparasite of the genus Amyloodinium.

13. The method according to claim 12, wherein the amoeba is of the genus Neoparamoeba or is Neoparamoeba perurans; wherein the ectoparasite of the genus *Gyrodactylus* is *Gyrodactylus salaris*; wherein the ectoparasite of the genus Cryptocaryon is Cryptocaryon *irritans*; and/or wherein the ectoparasite of the genus *Lernaeocera* is *Lernaeocera branchialis*.

14. The method according to claim 1, wherein said probiotic composition is administered in combination with a chemical parasitic infection treatment agent.

15. The method according to claim 14, wherein the chemical parasitic infection treatment agent is an organophosphate, a carbamate, a pyrethroid, a pyrethrin, an insect growth regulating chemical and/or an avermectin.

16. The method according to claim 1, wherein said probiotic composition is administered via bath or dip administration in salt, fresh or brackish water, by oral administration, or injection.

17. The method according to claim 16, wherein the bath administration is for a time period of from 1 second to 5 hours; from 1 second to 2 hours; from 1 second to 1 hour; from 30 seconds to 1 hour; or from 1 minute to 30 minutes.

18. The method according to claim 1, wherein said probiotic composition is administered at least 10 days before exposure of the teleost to the ectoparasite and/or gill parasite.

19. The method according to claim 18, wherein said probiotic composition is administered at least 15 days, 20 days, 25 days, 30 days, or 40 days, before exposure of the teleost to the ectoparasite and/or gill parasite.

* * * * *